United States Patent
Arzi et al.

(10) Patent No.: US 12,318,550 B2
(45) Date of Patent: *Jun. 3, 2025

(54) DEVICE AND METHOD FOR CONTROLLING RESPIRATION DURING SLEEP

(71) Applicant: Yeda Research and Development Co. Ltd., Rehovot (IL)

(72) Inventors: Anat Arzi, Rehovot (IL); Lee Sela, Rehovot (IL); Anton Plotkin, Rehovot (IL); Aharon Weissbrod, Rehovot (IL); Noam Sobel, Jaffa (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 17/975,625

(22) Filed: Oct. 28, 2022

(65) Prior Publication Data

US 2023/0055651 A1    Feb. 23, 2023

Related U.S. Application Data

(63) Continuation of application No. 16/545,007, filed on Aug. 20, 2019, now Pat. No. 11,491,301, which is a
(Continued)

(51) Int. Cl.
*A61M 21/00* (2006.01)
*A61M 15/08* (2006.01)
(Continued)

(52) U.S. Cl.
CPC .......... *A61M 21/02* (2013.01); *A61M 15/085* (2014.02); *A61M 16/10* (2013.01);
(Continued)

(58) Field of Classification Search
CPC ........ A61M 2021/00; A61M 2021/005; A61M 2021/0016; A61M 2021/0083; A61M 2021/02

See application file for complete search history.

(56) References Cited

U.S. PATENT DOCUMENTS

| | | | |
|---|---|---|---|
| 5,725,472 A | 3/1998 | Weathers | |
| 5,819,347 A | 10/1998 | Masuda | |

(Continued)

FOREIGN PATENT DOCUMENTS

| | | |
|---|---|---|
| DE | 19853394 | 5/2000 |
| JP | 2006-325756 | 12/2006 |
| WO | WO 2010/100567 | 9/2010 |

OTHER PUBLICATIONS

Advisory Action Before the Filing of An Appeal Brief Dated Jun. 8, 2017 From the US Patent and Trademark Office Re. U.S. Appl. No. 13/520,581. (4 Pages).
(Continued)

*Primary Examiner* — LaToya M Louis

(57) ABSTRACT

A device for controlling respiration during sleep based on the user physiological characteristic. The device includes an odor disperser for dispersing an odor; at least one detector for detecting a physiological characteristic of a user; and a controller for controlling respiration of the user by instructing the odor dispenser to disperse an odor responsive to detections by the at least one detector.

17 Claims, 10 Drawing Sheets

Related U.S. Application Data continuation of application No. 13/520,581, filed as application No. PCT/IL2011/000011 on Jan. 5, 2011, now Pat. No. 10,456,550.

(60) Provisional application No. 61/282,233, filed on Jan. 5, 2010.

(51) Int. Cl.
  *A61M 16/10* (2006.01)
  *A61M 21/02* (2006.01)

(52) U.S. Cl.
  CPC .............. *A61M 2021/0016* (2013.01); *A61M 2021/0088* (2013.01); *A61M 2205/3375* (2013.01); *A61M 2230/40* (2013.01); *A61M 2230/63* (2013.01)

(56) References Cited

U.S. PATENT DOCUMENTS

| | | | |
|---|---|---|---|
| 6,093,158 | A | 7/2000 | Morris |
| 6,198,963 | B1 * | 3/2001 | Haim .............. A61B 17/22012 600/431 |
| 6,467,477 | B1 | 10/2002 | Frank et al. |
| 10,456,550 | B2 | 10/2019 | Arzi et al. |
| 2001/0042546 | A1 | 11/2001 | Umeda et al. |
| 2004/0079814 | A1 | 4/2004 | Altadonna, Jr. |
| 2005/0283039 | A1 | 12/2005 | Cornel |
| 2007/0023044 | A1 | 2/2007 | Kwok et al. |
| 2007/0083079 | A1 | 4/2007 | Lee et al. |
| 2008/0041373 | A1 | 2/2008 | Doshi et al. |
| 2008/0227857 | A1 | 9/2008 | Wei |
| 2008/0308106 | A1 | 12/2008 | Augustine et al. |
| 2012/0078065 | A1 | 3/2012 | De Lemos et al. |
| 2012/0272958 | A1 | 11/2012 | Arzi et al. |
| 2020/0046935 | A1 | 2/2020 | Arzi et al. |

OTHER PUBLICATIONS

Communication Pursuant to Article 94(3) EPC Dated Apr. 18, 2019 From the European Patent Office Re. Application No. 11701161.9. (9 Pages).
Communication Pursuant to Article 94(3) EPC Dated Jan. 18, 2017 From the European Patent Office Re. Application No. 11701161.9. (7 Pages).
Communication Pursuant to Article 94(3) EPC Dated Sep. 22, 2020 From the European Patent Office Re. Application No. 11701161.9. (5 Pages).
Communication Pursuant to Article 94(3) EPC Dated Nov. 27, 2019 From the European Patent Office Re. Application No. 11701161.9. (14 Pages).
European Search Report and the European Search Opinion Dated Jan. 19, 2022 From the European Patent Office Re. Application No. 21169309.8. (9 Pages).
Examiners Answer Dated Dec. 4, 2018 Before The Patent Trial and Appeal Board of the US Patent and Trademark Office Re. U.S. Appl. No. 13/520,581. (10 pages).
Examiners Answer Dated Nov. 24, 2017 Before The Patent Trial and Appeal Board of the US Patent and Trademark Office Re. U.S. Appl. No. 13/520,581. (20 pages).
International Preliminary Report on Patentability Dated Jul. 19, 2012 From the International Bureau of WIPO Re. Application No. PCT/IL2011/000011.
International Search Report and the Written Opinion Dated May 20, 2011 From the International Searching Authority Re. Application No. PCT/IL2011/000011.
Notice of Allowance Dated Jul. 7, 2022 from US Patent and Trademark Office Re. U.S. Appl. No. 16/545,007. (10 pages).
Notice Of Allowance Dated Mar. 21, 2019 From the US Patent and Trademark Office Re. U.S. Appl. No. 13/520,581. (3 pages).

Office Action Dated Nov. 10, 2014 From the Israel Patent Office Re. Application No. 220798.
Office Action Dated Feb. 15, 2015 From the Israel Patent Office Re. Application No. 220798.
Office Action Dated May 19, 2015 From the Israel Patent Office Re. Application No. 220798.
Official Action Dated Feb. 2, 2016 From the US Patent and Trademark Office Re. U.S. Appl. No. 13/520,581.
Official Action Dated Jul. 17, 2015 From the US Patent and Trademark Office Re. U.S. Appl. No. 13/520,581.
Official Action Dated Jan. 21, 2022 from US Patent and Trademark Office Re. U.S. Appl. No. 16/545,007. (19 pages).
Official Action Dated May 27, 2016 From the US Patent and Trademark Office Re. U.S. Appl. No. 13/520,581.
Official Action Dated Dec. 30, 2016 From the US Patent and Trademark Office Re. U.S. Appl. No. 13/520,581. (18 pages).
Second Notice Of Allowance Dated Aug. 9, 2019 From the US Patent and Trademark Office Re. U.S. Appl. No. 13/520,581. (6 pages).
Translation Dated Mar. 1, 2015 of Office Action Dated Feb. 15, 2015 From the Israel Patent Office Re. Application No. 220798.
Arzi et al. "The Influence of Odorants on Respiratory Patterns in Sleep", Chemical Senses, 35(1):31-40, XP55071862A, Nov. 16, 2009.
Atlas Task Force "EEG Arousals: Scoring Rules and Examples", Atlas Task Force of the American Sleep Disorders Association, ASDA Report, Sleep, 15(2): 173-184, 1992.
Badia et al. "Responsiveness to Olfactory Stimuli Presented in Sleep", Physiology & Behavior, 48: 87-90, 1990.
Ballester et al. "Evidence of the Effectiveness of Continuous Positive Airway Pressure in the Treatment of Sleep Apnea/Hypopnea Syndrome", American Journal of Respiratory and Critical Care Medicine, 159: 495-501, 1999.
Bensafi et al. "Hedonic-Specific Activity in Piriform Cortex During Odor Imagery Mimics That During Odor Perception", Journal of Neurophysiology, 98: 3254-3262, Oct. 3, 2007.
Brunner "Success and Failure of Mirtazapine as Alternative Treatment in Elderly Stroke Patients With Sleep Apnea—A Preliminary Open Trial", Sleep Breath, 12: 281-285, Published Online Mar. 28, 2008.
Carley et al. "Efficacy of Mirtazapine in Obstructive Sleep Apnea Syndrome", Sleep, 30(1): 35-41, 2007.
Charuzi et al. "Bariatric Surgery in Morbidly Obese Sleep-Apnea Patients: Short- and Long-Term Follow-Up", American Journal of Clinical Nutrition, 55: 594S-596S, 1992.
Doty et al. "Intranasal Trigeminal Stimulation From Odorous Volatiles: Psychometric Responses From Anosmic and Normal Humans", Physiology & Behavior, 20: 175-185, 1978.
Eckert et al. "Mechanisms of Apnea", Progress in Cardiovascular Diseases, 51(4): 313-323, Jan./Feb. 2009.
Ferini-Strambi et al. "Cognitive Dysfunction in Patients With Obstructive Sleep Apnea (OSA): Partial Reversibility After Continuous Positive Airway Pressure (CPAP)", Brain Research Bulletin, 61: 87-92, 2003.
Field et al. "Lavender Bath Oil Reduces Stress and Crying and Enhances Sleep in Very Young Infants", Early Human Development, 84: 399-401, 2008.
Fitzpatrick et al. "Partitioning of Inhaled Ventilation Between the Nasal and Oral Routes During Sleep in Normal Subjects", Journal of Applied Physiology, 94: 883-890, 2003.
Fontanini et al. "Slow-Waves in the Olfactory System: An Olfactory Perspective on Corticol Rhythms", Trands in Neuroscience, 29(8): 29(8): 429-437, Published Online Jul. 13, 2006.
Goel et al. "An Olfactory Stimulus Modifies Nighttime Sleep in Young Men and Women", Chronobiology International, 22(5): 889-904, 2005.
Goel et al. "Sleep Changes Vary by Odor Perception in Young Adults", Biological Psychology, 71: 341-349, 2006.
Grupp et al. "Chemosensory Induced Arousals During Sleep in Premenopausal Women", Neuroscience Letters, 444: 22-26, 2008.

(56) References Cited

OTHER PUBLICATIONS

Hummel et al. "Intranasal Chemosensory Function of the Trigeminal Nerve and Aspects of Its Relation to Olfaction", International Archives of Occupational and Environmental Health, 75(5): 305-313, Epub Mar. 2, 2002.
Issa et al. "Upper Airway Closing Pressures in Obstructive Sleep Apnea", Journal of Applied Physiology, 57: 520-527, 1984.
Johnson et al. "A Comparison of Methods for Sniff Measurement Concurrent With Olfactory Tasks in Humans", Chemical Senses, 31: 795-806, Advance Access Publication Aug. 16, 2006.
Johnson et al. "Methods for Building An Olfactometer With Known Concentration Outcomes", Journal of Neuroscience Methods, 160: 231-245, 2007.
Johnson et al. "Rapid Olfactory Processing Implicates Subcortical Control of An Olfactomotor System", Journal of Neurophysiology, 90: 1084-1094, First Published Apr. 23, 2003.
Lewith et al. "A Single-Blinded, Randomized Pilot Study Evaluating the Aroma of Lavandula Augustifolia as A Treatment for Mild Insomnia", The Journal of Alternative and Complementary Medicine, 11(4): 631-637, 2005.
Liao et al. "Incidence and Severity of Obstructive Sleep Apnea Following Pharyngeal Flap Surgery in Patients With Cleft Palate", The Cleft Palate-Craniofacial Journal, 39(3): 312-316, May 2002.
Marin et al. "Long-Term Cardiovascular Outcomes in Men With Obstructive Sleep Apnoea-Hypopnoea With or Without Treatment With Continuous Positive Airway Pressure: An Observational Study", The Lancet, 365: 1046-1053, Mar. 19, 2005.
Marlier et al. "Olfactory Stimulation Prevents Apnea in Premature Newborns", Pediatrics, 115(1): 83-88, 2005.
Mortimore et al. "Palatal Muscle EMG Response to Negaive Pressure in Awake Sleep Apneic and Control Subjects", American Journal of Respiratory and Critical Care Medicine, 156: 867-873, 1997.
Nelesen et al. "Continuous Positive Airway Pressure Normalizes Cardiac Autonomic and Hemadynamic Responses to Laboratory Stressor in Apneic Patients", Chest, 119: 1092-1101, 2001.
Pepin et al. "Side Effects of Nasal Continuous Positive Airway Pressure in Sleep Apnea Syndrome. Study of 193 Patients in Two French Sleep Centers", Chest, 107(2): 375-381, Feb. 1995.
Punjabi et al. "Sleep-Disordered Breathing, Glucose Intolerance, and Insulin Resistance. The Sleep Heart Health Study", American Journal of Epidemiology, 160(6): 521-530, 2004.
Rasch et al. "Odor Cues During Slow-Wave Sleep Prompt Declarative Memory Consolidation", Science, 315: 1426-1429, Mar. 9, 2007.
Sano et al. "Influence of Cedar Essence on Spontaneous Activity and Sleep of Rats and Human Daytime Nap", Psychiatry and Clinical Neurosciences, 52: 133-135, 1998.
Seelke et al. "Sniffing in Infant Rats During Sleep and Wakefulness", Bahavioral Neuroscience, 118(2): 267-273, 2004.
Sobel et al. "A Method for Functional Magnetic Resonance Imaging of Olfaction", Journal of Neuroscience Methods, 78: 115-123, 1997.
Sobel et al. "Blind Smell: Brain Activation Induced by An Undetected Air-Borne Chemical", Brain, 122(Pt.2): 209-217, 1999.
Stuck et al. "Arousal Responses to Olfacory or Trigeminal Stimulation During Sleep", Sleep, 30(4): 506-510, 2007.
Waldhorn et al. "Long-Term Compliance With Nasal Continuous Positive Airway Pressure Therapy of Obstructive Sleep Apnea", Chest, 97(1): 33-38, Jan. 1990.
Walker et al. "Human Responses to Propionic Acid. II. Quantification of Breathing Responses and Their Relationship to Perception", Chemical Senses, 26: 351-358, 2001.
Young et al. "The Occurrence of Sleep-Disordered Breathing Among Middle-Aged Adults", The New England Journal of Medicine, 328(17): 1230-1235, Apr. 29, 1993.
Youngentob et al. "A Quantitative Analysis of Sniffing Strategies in Rats Performing Odor Detection Tasks", Physiology & Behavior, 41: 59-69, 1987.

\* cited by examiner

Table 1 Wakes and arousal occurrence during odorant presentation and baseline

| | Wakes frequency | | Arousal frequency | |
|---|---|---|---|---|
| Odor/sleep stage | Vanillin baseline | Vanillin | Vanillin baseline | Vanillin |
| Stage 2 | 1.4 ± 2.5% | 2.2 ± 5.2% | 5.2 ± 8.9% | 2.6 ± 4.8% |
| SWS | 4.2 ± 14.4% | 0 ± 0% | 9.1 ± 7.8% | 2.8 ± 9.6% |
| REM | 3.8 ± 7.8% | 0 ± 0% | 4.4 ± 10.8% | 0 ± 0% |
| All stages | 3.1 ± 9.4% | 0.7 ± 3.1% | 10.4 ± 12.1% | 1.8 ± 6.2% |
| Odor/sleep stage | Lavender oil baseline | Lavender oil | Lavender oil baseline | Lavender oil |
| Stage 2 | 3.8 ± 3.9% | 7.0 ± 7.6% | 4.0 ± 4.2% | 9.5 ± 8.8% |
| SWS | 6.9 ± 10.8% | 0 ± 0% | 4.2 ± 15.1% | 0 ± 0% |
| REM | 6.7 ± 13.5% | 0 ± 0% | 0 ± 0% | 0 ± 0% |
| All stages | 5.8 ± 9.8% | 2.3 ± 5.4% | 2.7 ± 8.4% | 3.2 ± 6.7% |
| Odor/sleep stage | Ammonium sulfide baseline | Ammonium sulfide | Ammonium sulfide baseline | Ammonium sulfide |
| Stage 2 | 0 ± 0% | 2.1 ± 4.7% | 1.9 ± 2.6% | 9.3 ± 10.9% |
| SWS | 0 ± 0% | 0 ± 0% | 4.0 ± 8.9% | 0 ± 0% |
| REM | 0 ± 0% | 0 ± 0% | 2.9 ± 6.4% | 5.0 ± 11.2% |
| All stages | 0 ± 0% | 0.7 ± 2.7% | 2.9 ± 6.1% | 4.8 ± 9.2% |
| Odor/sleep stage | Vetiver oil baseline | Vetiver oil | Vetiver oil baseline | Vetiver oil |
| Stage 2 | 0.8 ± 2.4% | 0 ± 0% | 7.3 ± 6.3% | 1.4 ± 3.6% |
| SWS | 0 ± 0% | 0 ± 0% | 6.2 ± 6.4% | 0 ± 0% |
| REM | 7.1 ± 18.9% | 0 ± 0% | 3.6 ± 9.4% | 4.1 ± 10.8% |
| All stages | 2.6 ± 10.9% | 0 ± 0% | 6.3 ± 9.2% | 1.8 ± 6.4% |

The percentage of odorant presentations accompanied by wakes or arousals by sleep stage and odorant. REM, rapid eye movement.

FIG. 7

Vanillin

Lavender

AmSu

Vetiver

Table 2  Respiration volume during odor presentation and baseline

| Breath/odor | Baseline | Breath 1 | Breath 2 | Breath 3 | Breath 4 | Breath 5 | Breath 6 |
|---|---|---|---|---|---|---|---|
| Inhale/exhale volume ratio | | | | | | | |
| Vanillin | 1.00 | 0.73 ± 0.08*** | 0.78 ± 0.07*** | 0.80 ± 0.07*** | 0.87 ± 0.08*** | 0.86 ± 0.1*** | 0.95 ± 0.09 |
| Lavender oil | 1.00 | 0.77 ± 0.09*** | 0.83 ± 0.06*** | 0.90 ± 0.07*** | 0.93 ± 0.05*** | 0.92 ± 0.06*** | 0.93 ± 0.07* |
| Ammonium sulfide | 1.00 | 0.74 ± 0.04*** | 0.80 ± 0.05*** | 0.88 ± 0.06* | 0.82 ± 0.09* | 0.94 ± 0.08 | 1.01 ± 0.08 |
| Vetiver oil | 1.00 | 0.74 ± 0.07*** | 0.81 ± 0.04*** | 0.87 ± 0.06* | 0.94 ± 0.06 | 0.95 ± 0.08 | 1.00 ± 0.04 |
| All odorants | 1.00 | 0.75 ± 0.08*** | 0.80 ± 0.06*** | 0.86 ± 0.08*** | 0.89 ± 0.08*** | 0.91 ± 0.08*** | 0.96 ± 0.08** |
| Inhalation volume (ml) | | | | | | | |
| Vanillin | 164.63 ± 62.96 | 126.33 ± 55.64*** | 132.54 ± 56.78*** | 136.05 ± 57.79*** | 140.76 ± 60.06*** | 142.77 ± 61.94*** | 146.49 ± 58.67* |
| Lavender oil | 138.21 ± 47.25 | 116.39 ± 48.86*** | 119.36 ± 50.62*** | 123.56 ± 48.52*** | 130.79 ± 50.92 | 129.96 ± 46.65** | 129.85 ± 49.85 |
| Ammonium sulfide | 229.24 ± 93.92 | 193.40 ± 94.90* | 196.22 ± 87.06 | 212.98 ± 92.53 | 195.75 ± 101.68 | 212.17 ± 94.47 | 217.90 ± 89.61 |
| Vetiver oil | 209.94 ± 84.00 | 185.48 ± 84.09* | 194.63 ± 82.12* | 202.08 ± 81.76 | 210.94 ± 81.50 | 215.34 ± 85.44 | 216.52 ± 84.80 |
| All odorants | 171.61 ± 72.01 | 141.92 ± 69.72*** | 146.98 ± 69.36*** | 153.23 ± 71.67*** | 156.50 ± 72.19*** | 159.88 ± 73.24*** | 162.07 ± 72.73** |
| Exhalation volume (ml) | | | | | | | |
| Vanillin | 164.63 ± 62.96 | 174.21 ± 71.71 | 167.87 ± 68.48 | 165.68 ± 64.72 | 160.11 ± 63.54 | 161.28 ± 62.38 | 155.94 ± 155.94 |
| Lavender oil | 138.21 ± 47.25 | 147.54 ± 54.66* | 143.29 ± 56.01 | 138.84 ± 51.90 | 139.79 ± 50.94 | 140.84 ± 47.41 | 137.09 ± 45.72 |
| Ammonium sulfide | 229.24 ± 93.93 | 256.93 ± 117.13 | 246.67 ± 107.19 | 238.39 ± 97.41 | 230.76 ± 99.54 | 222.07 ± 89.59 | 215.84 ± 95.11 |
| Vetiver oil | 209.94 ± 84.01 | 245.06 ± 104.99* | 239.31 ± 101.09* | 233.06 ± 100.94 | 229.69 ± 99.14 | 226.24 ± 93.14 | 217.34 ± 89.00 |
| All odorants | 171.62 ± 72.01 | 187.87 ± 87.71*** | 181.85 ± 84.30* | 177.32 ± 80.26 | 174.18 ± 78.67 | 173.17 ± 73.56 | 167.69 ± 72.78 |

Averages of inhale/exhale volume ratio, inhalation, and exhalation volume in 6 breaths after odor onset and baseline. Significance level of the comparison between baseline and after odor breath: *$P<0.05$; $P<0.005$; *$P<0.0005$.

FIG. 9

DEVICE AND METHOD FOR CONTROLLING RESPIRATION DURING SLEEP

RELATED APPLICATIONS

This application is a continuation of U.S. patent application Ser. No. 16/545,007 filed on Aug. 20, 2019, which is a is a continuation of U.S. patent application Ser. No. 13/520,581 filed on Jul. 5, 2012, now U.S. Pat. No. 10,456,550, which is a National Phase of PCT Patent Application No. PCT/IL2011/000011 having International Filing Date of Jan. 5, 2011, which claims the benefit of priority under 35 USC 119(e) of U.S. Provisional Patent Application No. 61/282,233 filed on Jan. 5, 2010. The contents of the above applications are all incorporated herein by reference in their entirety.

FIELD AND BACKGROUND OF THE INVENTION

The present invention, in some embodiments thereof, relates to dispersing odor during sleep and, more particularly, but not exclusively, to dispersing odor without inducing arousal.

The influence of odor on living beings has been greatly studied. A number of studies have also researched the influence of odor on living beings during sleep.

Badia et al (1990) assessed whether humans react to olfactory stimuli presented in sleep. Badia et al found that peppermint presentation of about 3 min to sleeping humans did not affect respiration during these 3 min in comparison to other sleeping periods.

Marlier at al. (2005) showed that the introduction of a pleasant odor in premature newborn's incubator is of therapeutic value in the treatment of apneas unresponsive to caffeine and doxapram.

Seelke and Blumberg (2004) examined whether sniffing and arousal are dissociable by presenting 8-day-old rats with dimethyl disulfide (DMDS) while monitoring respiration and behavioral state. It was found that sniffing, including polypnea, occurred while the rats were asleep. Seelke and Blumberg also noted that presentation of DMDS did not evoke reliable arousal responses in the sleeping rats.

Stuck et al (2007) found that the presentation of a strong but selective olfactory stimulus does not lead to arousals during nocturnal sleep in humans. In contrast, Stuck et al found that stimulation with a selective trigeminal irritant, CO2, produced a concentration-dependent increase in arousal frequency.

Additional Background Art Includes

AAoSMTF. 1992. EEG arousals: scoring rules and examples: a preliminary report from the Sleep Disorders Atlas Task Force of the American SleepDisorders Association. Sleep. 15:173-184;

AAoSMTF. 1999. Sleep-related breathing disorders in adults: recommendations for syndrome definition and measurement techniques in clinical research. The report of an American Academy of Sleep Medicine Task Force. Sleep. 22:667-689;

Badia P, Wesensten N, Lammers W, Culpepper J, Harsh J. 1990. Responsiveness to olfactory stimuli presented in sleep. Physiol Behay. 48:87-90;

Ballester E, Badia J R, Hernandez L, Carrasco E, de Pablo J, Fornas C, Rodriguez-Roisin R, Montserrat J M. 1999. Evidence of the effectiveness of continuous positive airway pressure in the treatment of sleep apnea/hypopnea syndrome. Am J Respir Crit Care Med. 159:495-501.;

Bedard M A, Montplaisir J, Richer F, Rouleau I, Malo J. 1991. Obstructive sleep apnea syndrome: pathogenesis of neuropsychological deficits. J Clin Exp Neuropsychol. 13:950-964.;

Bensafi M, Sobel N, Khan R M. 2007. Hedonic-specific activity in piriform cortex during odor imagery mimics that during odor perception. J Neurophysiol. 98:3254-3262.;

Brunner H. 2008. Success and failure of mirtazapine as alternative treatment in elderly stroke patients with sleep apnea—a preliminary open trial. Sleep Breath. 12:281-285.;

Carley D W, Olopade C, Ruigt G S, Radulovacki M. 2007. Efficacy of mirtazapine in obstructive sleep apnea syndrome. Sleep. 30:35-41.; Carskadon M A, Herz R S. 2004. Minimal olfactory perception during sleep: why odor alarms will not work for humans. Sleep. 27:402-405.;

Charuzi I, Lavie P, Peiser J, Peled R. 1992. Bariatric surgery in morbidly obese sleep-apnea patients: short- and long-term follow-up. Am J Clin Nutr. 55:594S-596S.;

Chesson A L Jr., Ferber R A, Fry J M, Grigg-Damberger M, Hartse K M, Hurwitz T D, Johnson S, Kader G A, Littner M, Rosen G, et al. 1997. The indications for polysomnography and related procedures. Sleep. 20:423-487.;

Doty R L, Brugger W E, Jurs P C, Orndorff M A, Snyder P J, Lowry L D. 1978. Intranasal trigeminal stimulation from odorous volatiles: psychometric responses from anosmic and normal humans. Physiol Behay. 20: 175-185.;

Eckert D J, Malhotra A, Jordan A S. 2009. Mechanisms of apnea. Prog Cardiovasc Dis. 51:313-323.;

Ferini-Strambi L, Baietto C, Di Gioia M R, Castaldi P, Castronovo C, Zucconi M, Cappa S F. 2003. Cognitive dysfunction in patients with obstructive sleep apnea (OSA): partial reversibility after continuous positive airway pressure (CPAP). Brain Res Bull. 61:87-92.;

Field T, Cullen C, Largie S, Diego M, Schanberg S, Kuhn C. 2008. Lavender bath oil reduces stress and crying and enhances sleep in very young infants. Early Hum Dev. 84:399-401.;

Fitzpatrick M F, Driver H S, Chatha N, Voduc N, Girard A M. 2003. Partitioning of inhaled ventilation between the nasal and oral routes during sleep in normal subjects. J Appl Physiol. 94:883-990.;

Fleisher K E, Krieger A C. 2007. Current trends in the treatment of obstructive sleep apnea. J Oral Maxillofac Surg. 65:2056-2068.;

Fontanini A, Bower J M. 2006. Slow-waves in the olfactory system: an olfactory perspective on cortical rhythms. Trends Neurosci. 29:429-437.;

Goel N, Kim H, Lao R P. 2005. An olfactory stimulus modifies nighttime sleep in young men and women. Chronobiol Int. 22:889-904.;

Goel N, Lao R P. 2006. Sleep changes vary by odor perception in young adults. Biol Psychol. 71:341-349.;

Grupp K, Maurer J T, Hormann K, Hummel T, Stuck B A. 2008. Chemosensory induced arousals during sleep in premenopausal women. Neurosci Lett. 444:22-26.;

Hummel T, Livermore A. 2002. Intranasal chemosensory function of the trigeminal nerve and aspects of its relation to olfaction. Int Arch Occup Environ Health. 75:305-313.;

Issa F G, Sullivan C E. 1984. Upper airway closing pressures in obstructive sleep apnea. J Appl Physiol. 57:520-527.;

Johnson B N, Mainland J D, Sobel N. 2003. Rapid olfactory processing implicates subcortical control of an olfactomotor system. J Neurophysiol. 90:1084-1094.;

Johnson B N, Russell C, Khan R M, Sobel N. 2006. A comparison of methods for sniff measurement concurrent with olfactory tasks in humans. Chem Senses. 31:795-806.;

Johnson B N, Sobel N. 2007. Methods for building an olfactometer with known concentration outcomes. J Neurosci Methods. 160:231-245.;

Kribbs N B, Pack A I, Kline L R, Smith P L, Schwartz A R, Schubert N M, Redline S, Henry J N, Getsy J E, Dinges D F. 1993. Objective measurement of patterns of nasal CPAP use by patients with obstructive sleep apnea. Am Rev Respir Dis. 147:887-895.;

Lewith G T, Godfrey A D, Prescott P. 2005. A single-blinded, randomized pilot study evaluating the aroma of *Lavandula augustifolia* as a treatment for mild insomnia. J Altern Complement Med. 11:631-637.;

Liao Y F, Chuang M L, Chen P K, Chen N H, Yun C, Huang C S. 2002. Incidence and severity of obstructive sleep apnea following pharyngeal flap surgery in patients with cleft palate. Cleft Palate Craniofac J. 39:312-316.;

Marin J M, Carrizo S J, Vicente E, Agusti A G. 2005. Long-term cardiovascular outcomes in men with obstructive sleep apnoea-hypopnoea with or without treatment with continuous positive airway pressure: an observational study. Lancet. 365:1046-1053.;

Marlier L, Gaugler C, Messer J. 2005. Olfactory stimulation prevents apnea in premature newborns. Pediatrics. 115:83-88.;

Mortimore I L, Douglas N J. 1997. Palatal muscle EMG response to negative pressure in awake sleep apneic and control subjects. Am J Respir Crit Care Med. 156:867-873.; Murakami M, Kashiwadani H, Kirino Y, Mori K. 2005. State-dependent sensory gating in olfactory cortex. Neuron. 46:285-296.;

Nelesen R A, Yu H, Ziegler M G, Mills P J, Clausen J L, Dimsdale J E. 2001. Continuous positive airway pressure normalizes cardiac autonomic and hemodynamic responses to a laboratory stressor in apneic patients. Chest. 119:1092-1101.;

Pepin J L, Leger P, Veale D, Langevin B, Robert D, Levy P. 1995. Side effects of nasal continuous positive airway pressure in sleep apnea syndrome. Study of 193 patients in two French sleep centers. Chest. 107:375-381.;

Punjabi N M, Shahar E, Redline S, Gottlieb D J, Givelber R, Resnick H E. 2004. Sleep-disordered breathing, glucose intolerance, and insulin resistance: the Sleep Heart Health Study. Am J Epidemiol. 160:521-530.

Rasch B, Buchel C, Gais S, Born J. 2007. Odor cues during slow-wave sleep prompt declarative memory consolidation. Science. 315:1426-1429.;

Rechtschaffen A, Kales A. 1968. A manual of standardized terminology, techniques and scoring system for sleep stages of human subject. Washington: US Government Printing Office, National Institute of Health Publication.;

Sano A, Sei H, Seno H, Morita Y, Moritoki H. 1998. Influence of cedar essence on spontaneous activity and sleep of rats and human daytime nap. Psychiatry Clin Neurosci. 52:133-135.;

Seelke A M, Blumberg M S. 2004. Sniffing in infant rats during sleep and wakefulness. Behav Neurosci. 118:267-273.;

Sobel N, Prabhakaran V, Desmond J E, Glover G H, Sullivan E V, Gabrieli J D. 1997. A method for functional magnetic resonance imaging of olfaction. J Neurosci Methods. 78:115-123.;

Sobel N, Prabhakaran V, Hartley C A, Desmond J E, Glover G H, Sullivan E V, Gabrieli J D. 1999. Blind smell: brain activation induced by an undetected air-borne chemical. Brain. 122(Pt 2):209-217.;

Stuck B A, Stieber K, Frey S, Freiburg C, Hormann K, Maurer J T, Hummel T. 2007. Arousal responses to olfactory or trigeminal stimulation during sleep. Sleep. 30:506-5101;

Waldhorn R E, Herrick T W, Nguyen M C, O'Donnell A E, Sodero J, Potolicchio S J. 1990. Long-term compliance with nasal continuous positive airway pressure therapy of obstructive sleep apnea. Chest. 97:33-38.;

Walker J C, Kendal-Reed M, Hall S B, Morgan W T, Polyakov V V, Lutz R W. 2001. Human responses to propionic acid. II. Quantification of breathing responses and their relationship to perception. Chem Senses. 26:351-358.;

Warren D W, Walker J C, Drake A F, Lutz R W. 1994. Effects of odorants and irritants on respiratory behavior. Laryngoscope. 104:623-626.;

Young T, Palta M, Dempsey J, Skatrud J, Weber S, Badr S. 1993. The occurrence of sleep-disordered breathing among middle-aged adults. N Engl J Med. 328:1230-1235; and Youngentob S L, Mozell M M, Sheehe P R, Hornung D E. 1987. A quantitative analysis of sniffing strategies in rats performing odor detection tasks Physiol Behav. 41:59-69.

SUMMARY OF THE INVENTION

An aspect of some embodiments of the invention refers to controlling respiration during sleep. In some embodiments, respiration is controlled by repeated dispersion of odors. In some embodiments, respiration is controlled in a manner which thereby stops or prevents snoring and/or an apnea event. In some embodiment respiration is controlled by reducing the probability of snoring and/or apnea during a sleep period. Optionally, respiration is controlled to treat insomnia. Optionally, respiration is controlled without inducing arousal.

According to an aspect of some embodiments of the present invention there is provided a method of controlling respiration, the method comprising:

repeatedly dispersing an odor towards a sleeper during a sleep period;

controlling respiration of the sleeper by the repeatedly dispersing odor.

According to some embodiments of the invention, the method further comprises monitoring physiological characteristics of the sleeper during the sleep period.

According to some embodiments of the invention, monitoring physiological characteristics comprises monitoring respiration sounds. According to some embodiments of the invention, monitoring physiological characteristics comprises monitoring respiration movements. According to some embodiments of the invention, monitoring physiological characteristics comprises monitoring arousal. According to some embodiments of the invention, monitoring physiological characteristics comprises monitoring respiratory responses to the dispersing.

According to some embodiments of the invention, at least one dispersion of the repeatedly dispersing an odor is responsive to the monitoring.

According to some embodiments of the invention, the method further comprises selecting an odor for dispersion responsive to the monitoring. According to some embodiments of the invention, the method further comprises selecting a time length of odor dispersion responsive to the monitoring.

According to some embodiments of the invention, controlling respiration comprises preventing snoring. According to some embodiments of the invention, controlling respiration comprises preventing an apnea event. According to some embodiments of the invention, controlling respiration comprises controlling respiration without inducing arousal. According to some embodiments of the invention, controlling respiration comprises increasing inhalation of at least one breath following odor dispersion.

According to an aspect of some embodiments of the present invention there is provided a device for controlling respiration during sleep, the device comprising:

an odor disperser adapted to disperse an odor;
at least one detector adapted to detect a physiological characteristic of a user;
a controller configured for controlling respiration of the user by instructing the odor dispenser to disperse an odor responsive to detections by the at least one detector.

According to some embodiments of the invention, the controller is further configured for controlling respiration of the user over a sleep period by repeatedly instructing the odor dispersion to disperse an odor during the sleep period.

According to some embodiments of the invention, at least one detector is a sound detector. According to some embodiments of the invention, at least one detector is a respiration detector.

According to some embodiments of the invention, the controller is further configured for selecting an odor for dispersion. According to some embodiments of the invention, the controller is further configured for selecting a dose of odor for dispersion. According to some embodiments of the invention, the controller is configured to instruct odor dispersion, thereby preventing snoring by the user. According to some embodiments of the invention, the controller is configured to instruct odor dispersion, thereby preventing an apnea event by the user.

According to some embodiments of the invention, the device can be worn as a nose clip.

According to some embodiments of the invention, the device can be integrated into a bed pillow. According to some embodiments of the invention, the odors dispersed by the odor disperser control respiration of the user only.

According to an aspect of some embodiments of the present invention there is provided a method of controlling a device for controlling respiration of a user during sleep, the method comprising:

determining that respiration control by odor dispersion is desired;
providing a device for odor dispersion;
selecting a time period of odor dispersion responsive to the respiration control required; and
activating the device.

According to some embodiments of the invention, the method further comprises selecting an odorant for dispersion.

According to some embodiments of the invention, selecting is responsive to physiological measurements of a user.

According to some embodiments of the invention, the device is a device according to the aspect of some embodiments of the invention described above. According to some embodiments of the invention, the method further comprises monitoring odor influence on the user. According to some embodiments of the invention, selecting is responsive to the monitored influence.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 7 is a table of wake-ups and arousal occurrence during odorant presentation and baseline in an experiment according to some embodiments of the invention;

FIG. 9 is a table of respiration volume during odor presentation and baseline in an experiment according to some embodiments of the invention;

DESCRIPTION OF SPECIFIC EMBODIMENTS OF THE INVENTION

Figure 1:
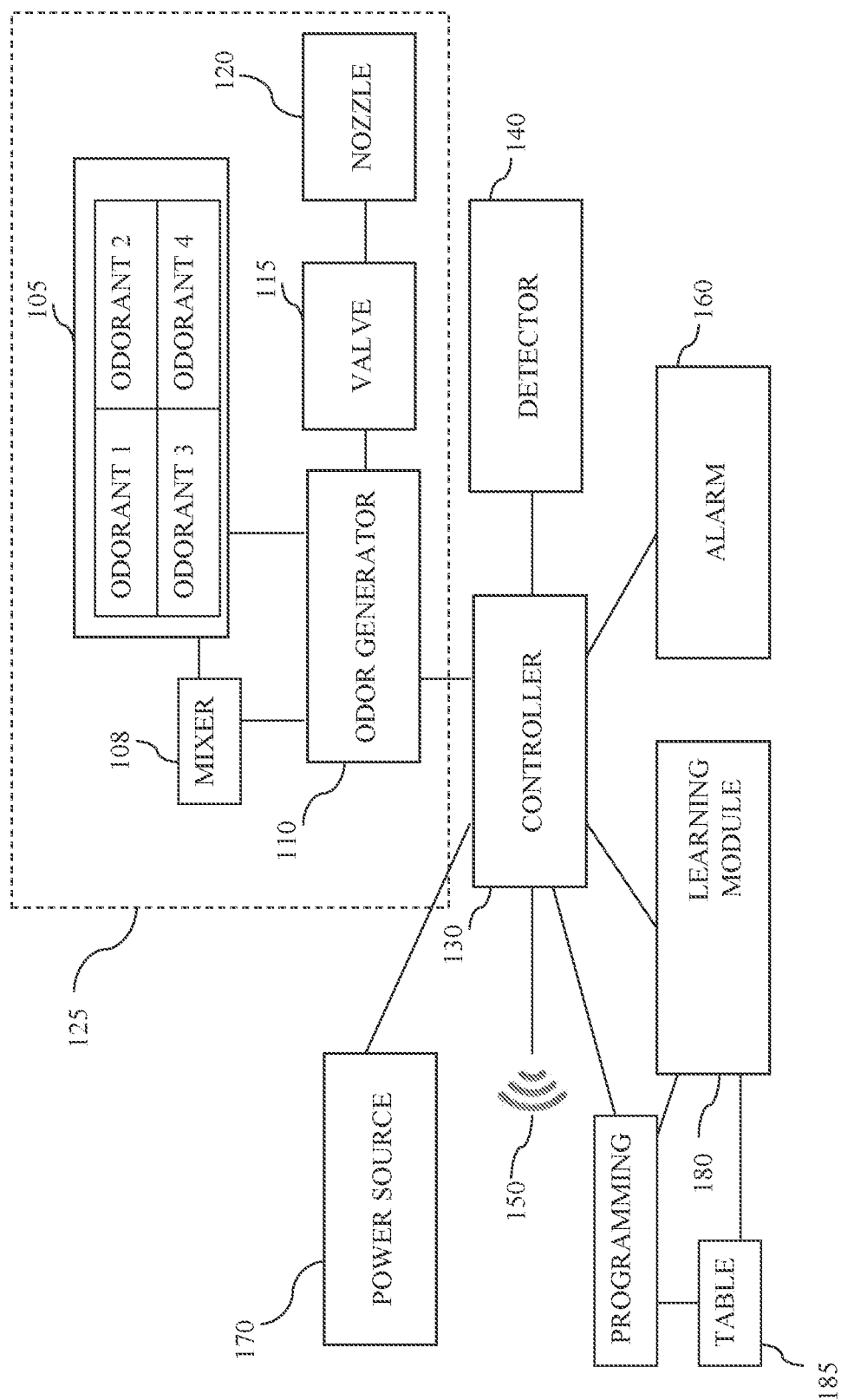
FIG. 1 is a block diagram of a device for controlling respiration in accordance with some embodiments of the invention.

The present invention, in some embodiments thereof, relates to dispersing odor during sleep and, more particularly, but not exclusively, to dispersing odor without inducing arousal.

An aspect of some embodiments of the invention relates to controlling respiration during sleep, optionally without inducing arousal or wake-up. In some embodiments, respiration is controlled by repeated dispersions of odor.

As used herein, the term "repeated dispersion" refers to two or more separate dispersions of odors during a single sleep period. Optionally, two or more separate dispersion of odors during a single sleep stage. Optionally, a sleep period is about 1-2 hours, or a night sleep of between 6-10 hours, such as 8 hours. In some embodiments, the delay between the beginnings of two consecutive dispersions of odors is between 3-30 min, or any intermediate number, for example dispersion of odor every 6, 9, 12 or 15 min. In some embodiments, each dispersion occurs for between 1-30 seconds, for example for 5, 10 or 20 seconds. Optionally, repeated dispersion refers to between 10-40, such as between 20-40, 15-35 or 20-30 dispersions of odor during a night sleep. Optionally, repeated dispersion continues till waking up of the user.

The inventors of the present application have found that repeated inhalation of odors during sleep may be used to control respiration. For example, the inhalation of certain odors decreases inhalation volume and increases exhalation volume, for several breaths, without inducing arousal or wake-up. The inventors have found that repeated application of odor dispersion can change a respiratory pattern during sleep without inducing arousal or wake-up As used herein, "controlling respiration" refers to influencing a respiratory pattern. In some embodiments, controlling respiration refers to maintaining respiration within a range, for example a range of breathings within a time period or range of volume of breathings. Optionally, maintaining respiration within a range is achieved by dispersing odors when respiration is out or almost out of the range. Alternatively or additionally, controlling respiration refers to preventing certain respiratory events, such as respiratory events that are considered as disturbing or dangerous, for example, snoring, choking or breathing suspensions. Optionally, preventing respiratory events is achieved by dispersion of odors when such respiratory events occur or are about to occur. For example, controlling respiration may refer to reducing snoring during a sleep period In some embodiments, controlling respiration refers to control of respiratory sounds during sleep, such as sounds in the throat or nasal cavities; For example, preventing or stopping snoring by changing the respiratory pattern, optionally by dispersion of odors. In some embodiments, controlling respiration refers to treating breathing suspensions, such as by enforcing breathing; For example, enforcing respiration, optionally by odor dispersion, when an apnea event has started or when the sleeper is choking.

In some embodiments of the invention controlling respiration refers to influencing upcoming breathings, for example decreasing inhalation in one or more breath following odor dispersion. In some embodiments of the invention controlling respiration refers to influencing the probability of respiratory events during a sleep period. For example, reducing the probability of snoring or apnea during a sleep period, optionally by between 30%-70%, such as by about or more than 40%, 50%, 60% or more.

As used herein, arousal and wake-up are defined as known in the art. In some embodiments of the invention, arousal is defined by an abrupt change in Electroencephalogram (EEG) frequency and/or a brief increase in Electromyogram (EMG) for more than 3 seconds. In some embodiments of the invention, wake-up is defined by an abrupt change in Electroencephalogram (EEG) frequency and/or a brief increase in Electromyogram (EMG) for more than 15 seconds. These definitions of arousal or wake-up are defined by the atlas task force of the American Sleep Disorder Association (AAoSTMF 1992). Other definitions of arousal and/or wake-up may be used according to embodiments of the present invention, for example by measuring increase in EMG alone, or by measuring electrocardiogram (ECG).

In some embodiments, respiration is controlled by inducing arousal. For example, if dispersion of odor did not change the respiratory pattern as expected, arousal may be induced. Optionally, arousal is induced by dispersion of odor. Alternatively or additionally, arousal is induced by sound or vibration. In some embodiments of the invention, a short arousal may be induced and is not considered as disturbing or interrupting a sleep period. For example, arousal of about 5-10 seconds may be induced to change a respiratory pattern, and does not significantly disturb sleep.

In some embodiments of the invention, odors are dispersed at predefined time frames. Optionally, the time frames are equally apart from each other, such as every 3, 6 or 9 minutes. Alternatively, the odor is dispersed at random time frames. In other embodiments, odors are dispersed responsive to a respiration event or to a number of respiratory events. For example, odors may be dispersed responsive to sounds, such as snoring sounds or responsive to no sounds, such as when there is a breathing suspension. In some embodiments, odors are dispersed at random or predefined time frames and in addition responsive to respiration events.

Alternatively or additionally, odors are dispersed at time frames based on a history of respiratory responses or respiratory events of a sleeper. For example, when a respiratory event is known to occur every certain time, odors may be dispersed at or before the expected time of event. Alternatively or additionally, odors are dispersed according to rate of recovery of inhalation volume; For example, dispersion of odor is repeated when inhalation volume is recovered by about 50%.

In exemplary embodiments, one or more of the dispersed odors do not induce arousal or wake-up. In some embodiments, one or more of the dispersed odors have only an olfactory effect. In other embodiments, one or more of the dispersed odors are trigeminal, having a nervous effect as well or instead. Optionally, one or more of the dispersed odors are mild trigeminal and/or are provided in a small enough dosage to do not induce an arousal or wake-up response. Optionally, the same odor is dispersed during a single sleep period. Alternatively or additionally, different odors are dispersed at different time frames during the sleep period. Alternatively, one or more mix of odorants is dispersed at different time frames.

In some embodiments, the dose (or concentration) of odor dispersed is pre-defined and constant. In other embodiments, the dose of odor is randomly defined. In other embodiments, the dose of odor is dynamically changeable for example responsive to increase in arousal levels or responsive to respiration events. For example, increase in dose when snoring occurs or decrease when no specific respiration event is detected. In some embodiments each odorant has a threshold upon which it may induce arousal or wake-up and/or a threshold at which it induces a desired respiratory response. Optionally, doses above such thresholds are avoided.

In some embodiments, an odor's changing effect on respiration is measured during the sleep period and the type, dose and time of odor dispersed is adapted accordingly. For example, in order to compensate for user adaptation to the odor or for room saturation the dose of odor may be increased over time or the type of odor may be changed.

An aspect of some embodiments of the invention relates to a device for controlling respiration during sleep. In some embodiments, the device is operative to release odors at certain time periods. Optionally, the device includes one or more detectors for detecting physiological measurements and/or sleep characteristics such as noise, respiration, sleep stage and more. Optionally, the device releases odors responsive to detections by the detectors, for example responsive to detected noises.

In some embodiments, the odors released by the device do not induce arousal or wake-up. Optionally, some of the odors released by the device do induce arousal and are used following an odor dispersion that did not reach a desired effect. Alternatively or additionally, other arousal inducers are used, such as alarm.

In some embodiments of the invention, the device can be integrated with existing devices, such as bed lamp, pillow, garments, bedding, bed table, radio, alarm clock, etc. Optionally, the device can be used in other embodiments than bed sleep, for example in a car or lecture, when a person is snoring and disturbing others.

In some embodiments of the invention, the device is designed to release odors near, at (or in) the nose of the sleeper. Optionally, the odors are dispersed without causing discomfort to others located near the sleeper, such as a spouse. Optionally, the dispersed odors do not control respirations of other located near the sleeper. Optionally, the dispersed odors are sensed by others located near the user but are insufficient to affect respiration of others.

In some embodiments, the device comprises a controller for controlling the release of odors, optionally in order to control respiration of the user. Optionally, the controller controls the time frames at which odors are released. Optionally, the controller controls the dose of odor released. Optionally, the controller controls the type of odor released. Optionally, the controller controls the length of each odor release.

In some embodiments, the device comprises a table of odorants and their affect on user's respiration, optionally according to dose and/or sleep stage. Optionally, the table is updated during activation of device, for example after a number dispersion or after a predefined time. In some embodiments, the controller is programmable according to a number of rules by which it can control. For example, rules such as dispersion of odors at predefined time frames and/or predefined doses and/or predefined lengths. Optionally, the rules are selected responsive to the information in the table. Alternatively or additionally, calculation is performed to select a rule responsive to the information in the table and/or other information detected.

In some embodiments the controller is connected to the one or more detectors and controlling is performed responsive to inputs received from the one or more detectors.

In some embodiments, the device is manually controllable by a user. For example, the device may include a timer for activating the device for a certain time period, which can be set by a user. Optionally, the device automatically detects sleep and wake-up of the user and operates when the user is sleeping or during a certain sleep stage. Optionally, the device detects sleep by any of lack of movement in the room, snoring sound, entry into bed or light turn off. Optionally, wake-up is detected by movement of the user (i.e. getting out of bed), by alarm tune or according to breath detection. In some embodiments, a user may manually set the dose and/or type of odor dispersed. In some embodiments, a practitioner may define odor dispersion by the device in accordance with an ongoing treatment for a sleeper.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Referring now to the drawings, FIG. 1 is a block diagram of a device 100 for controlling respiration during sleep, showing various optional features as well. Device 100 includes an odor generator 110 which is connected to an odorant reservoir 105 and is adapted to generate one or more odors. In some embodiments, odorant reservoir 105 includes one or more odors, for example, 1, 2, 3, 4, 5, 6 or more odors.

Optionally, the odorants in reservoir 105 are olfactory odorants, such as vanillin and ammonium sulfide. Alternatively or additionally, reservoir 105 includes trigeminal odorants, optionally mild trigeminal odorants which do not induce arousal or wake-up, for example lavender oil and vetiver oil. Optionally, one or more of the odorants in reservoir 105 do not induce arousal or wake-up response at stage 2 or slow wave sleep. Optionally, one or more odorants in reservoir 105 reduce arousal or wake-up responses, in stage 1 sleep or in any sleep stage. Optionally, one or more odorants in reservoir are considered pleasant odorants such as vanillin, lavender or perfume. Optionally, one or more odorants in reservoir 105 are considered unpleasant odorants, such as ammonium sulfide, vetiver oil or rotten food.

In some embodiments a scale of pleasantness is provided with signs (such as olfactory or trigeminal) and a user (or practitioner) can choose along scale and of different signs.

In some embodiments, one or more odorants in reservoir 105 temporarily modify respiration when inhaled during sleep. Optionally, inhalation of one or more odorants in reservoir 105 provide a respiratory rejection type response such as decreased inhalation for several breaths after odor onset, for example between 1-10 breaths, such as for 3, 4, 5, 6, 7 or 8 breaths. Optionally, inhalation of one or more odorants in reservoir 105 provide a respiration response of increased exhalation for several breaths after odor onset, for example between 1-10 breaths, such as 1, 2, 3, 4, 5 or 6 breaths. In some embodiments, odor dispersion provides a decrease of between 20%-40%, such as about 30% in nasal inhalation/exhalation volume ration in the first breath after odor onset. Optionally, one or more odorants in reservoir 105 may change a balance between nasal and oral breathing, such as to increase nasal breathing. For example, odor dispersion may increase nasal exhalation, reflecting an increase in oral inhalation.

For example, inhalation of vanillin may reduce nasal inhalation/exhalation volume ration for about 27% at the first breath after odor onset, a volume which linearly decreases till about 5% at the sixth breath after odor onset. That is, the inhalation volume may decrease with about 23% and the exhalation volume may increase with about 6% at the first breath after vanillin dispersion.

In some embodiments, the odors in reservoir 105 are stored (or pre-pressurized) in a capsule or can. Optionally, the odors are in liquid form which evaporates or is pumped out of the can. Alternatively, the odors are in solid form and sublimate when released from the capsule or can. Optionally, the odors are stored in hermetically sealed capsules or cans having a nozzle and a threaded end which can be screwed to the odor generator. Optionally, the odorants are sold at any pharmacy.

In some embodiments, a capsule or can including a plurality of odorants can be acquired by a user, for example as a test kit. The user may then decide to acquire only specific odorants or type of odorants for further use. Optionally, the user may order a capsule or can including a plurality of odorants.

Odor generator 110 is adapted to generate odorants from the odors in reservoir 105. Optionally, the odors are generated from molecules or blends of odorants in reservoir 105. Optionally, the odors are generated from a mix of odorants in reservoir 105. In some embodiments, each odorant in reservoir 105 is connected by a tube to an optional mixer 108. Optionally, each tube also includes a valve (optionally controllable by controller 130) for regulating the desired dose of odorant. Different doses may be used for each odorant. The odorants are then optionally mixed in mixer 108 as known in the art. For example, if the odorants are solid, the mixer may blend the odorants. Alternatively, if the odorants are in liquid form, the mixer may shake the odorants. Mixer 108 may then transfer the mixed odors to generator 105. Alternatively, mixer 108 is situated in generator 105.

Optionally, the mixed odors are of the same type (olfactory or trigeminal). Alternatively, types of odors are mixed in the generated odor. Optionally, the mixed odors comprise both pleasant and unpleasant odors. Alternatively, the mixed odors comprise only pleasant or unpleasant odors. Optionally, a mix of unpleasant odors may result in a pleasant odor or vice versa.

Odor generator 110 is connected to a nozzle 120 which releases the odors. Nozzle 120 is optionally connected to a regulator such as a valve or dosemeter 115 for regulating the dose of odor dispersed. Optionally, the odors are released as a puff of air, optionally by use of a pump. Alternatively, a block of odorant is embedded within an airflow which is constantly released from nozzle 120. For example, odor can be mixed with air, resulting in an odor concentration of about 40%, 50%, 60% or more in the dispersed air. Alternatively, 100% of odor concentration is dispersed. Optionally, the regulator is an air dilution olfactometer, which is optionally computer-controlled. For example, an olfactometer as described in Sobel et al. 1997 or Johnson and Sobel, 1997, the disclosures of which are incorporated herein by reference. Optionally, a computer can control change in odor volume and/or odor concentration. Alternatively or additionally, the regulator is manually adjustable by a user or by a practitioner.

In some embodiments, valve 115 (or a pump at the odor source) provides an odor environment in which odors are not constantly dispersed but rather onset and offset of odorant delivery are perceived. In these embodiments, odor onset is designed to provide a change in odor concentration and to be sensed by the sleeper and optionally affects a respiratory pattern. In some embodiments, positioning valve 115 near nozzle 120 provides for better control of odor dispersion.

Nozzle 120 is optionally positioned near the nose of a sleeper which will inhale the odors. In some embodiments, nozzle 120 is directed towards the sleeper such that the dispersed odors will not cause discomfort to others located near the sleeper, such as a spouse sleeping near the sleeper. Optionally, the dispersed odors do not control or affect respiration of others located near the sleeper. In some embodiments, other located near the user sense a significantly lower dose of dispersed odors than sensed by the sleeper for which the device is designated. Optionally, only between 5%-50%, or less, of the released odors are sensed by others located near the user, for example only 10% or 20%. Optionally, the connection between nozzle 112 the odor generator or mixer is between 1 cm-2 meters, for example about 2 cm, 5 cm, 10 cm or 1-2 meters.

Figure 2A:
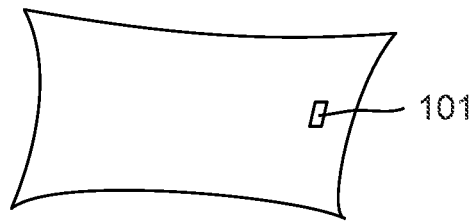
FIGS. 2A-2C are schematic illustrations of integrations of the device of FIG. 1, in accordance with exemplary embodiments of the invention.
Figure 2B:
Figure 2C:
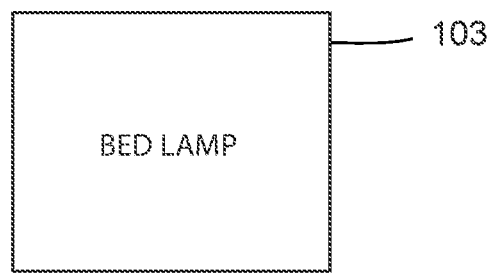

Optionally, nozzle 120 is positioned such that the odors are released in the nose of the sleeper. In some embodiments, nozzle 120 can be worn as a clip on a nose, a tube at or in the nose or as a nasal mask. Optionally, the nozzle is in the form of a clip which can be attached to headboard or pillow. In general, the distance of nozzle 120 from the nose of the user is a function of odor dosage, i.e. if the nozzle is positioned 1 cm from the nose of the user, a smaller dose of odor is needed than when the nozzle is positioned further away, such as 10 cm or more from the nose of the user. Different integrations of devices for controlling respiration during sleep according to embodiments of the invention are shown in FIGS. 2A-2C and described below.

Device 100 further optionally comprises one or more detectors 140 for detecting physiological measurements and/or sleep characteristics. In some embodiments, detector 140 detects sounds, such as sounds from the throat or the nasal which may indicate snoring or choking at certain noise levels. Optionally, detector 140 monitors breathing sounds. Optionally, the breathing sounds are recorded and analyzed using a sound data processing and recognition method. The device may thereby detect, any case of un-normal breathing event, for example breathing suspensions or snoring. In some embodiments, detector 140 detects the volume of breathing, such as shallow or deep breathings. In some embodiments, detectors 140 detect arousal or wake-up response, for example by electrodes that measure EEG and/or EMG. In some embodiments, detectors 140 detect the occurrence of an apnea event. In some embodiments, detector 140 is a breathing sensor which senses respiratory movements. In some embodiments, detector 140 detects at what sleep stage the sleeper is, for example by electrodes attached to the sleeper's head. In some embodiments, the detector detects blood oxygation and is optionally worn as a finger clip. Other detectors known in the art may also be used. Optionally, device 100 includes a plurality of detectors of different types.

Odor generator 110 and nozzle 120 are optionally connected to a controller 130. Controller 130 commands odor generator 110 to generate odors or a mix of odors and the dispersion of the generated odors by nozzle 120, optionally in order to control respiration of the user.

Figure 3:
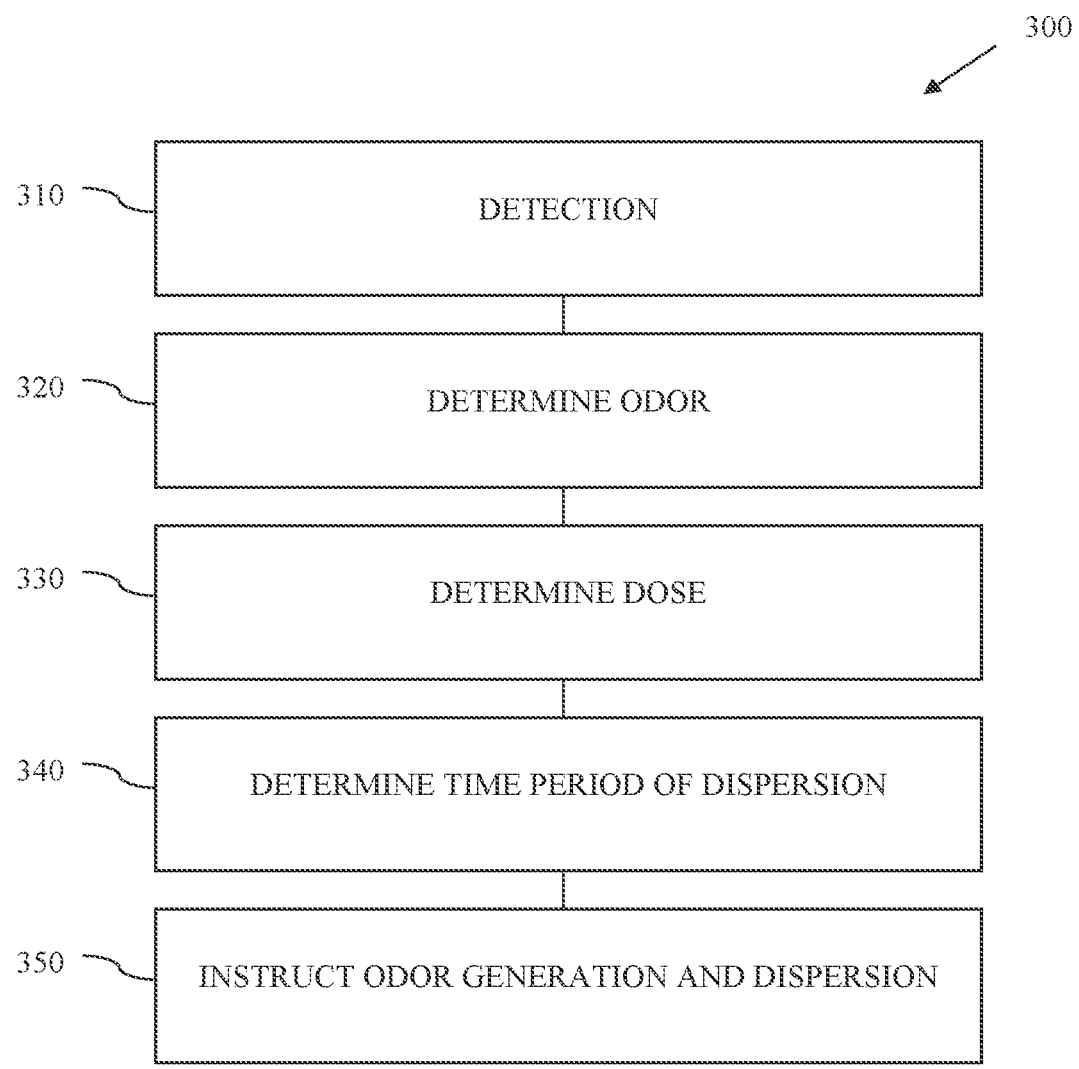
FIG. 3 is a flowchart of a method of controlling respiration by the device of FIG. 1 in accordance with some embodiments of the invention.

FIG. 3 is a flowchart of a method 300 of instructing odor generation and dispersion by controller 130, in accordance with some embodiments of the invention. In some embodiments, method 300 is not performed by a controller but manually, for example by a practitioner, such as a practitioner of method 400 described below.

At 310 controller 130 determines that an odor dispersion is necessary.

In some embodiments, controller 130 determines the necessity of odor dispersion according to predefined time frames. For example, controller 130 may determine the necessity of odor dispersion between every 3-30 min, for example every 6, 9, 12 or 15 min. optionally, controller determines the necessity of odor dispersion according to count of breaths, which is optionally limited to a number of breaths per minute. Optionally, controller 130 randomly determines the necessity of odor dispersion.

In some embodiments, controller 130 receives inputs from one or more detectors 140 and determines the necessity of odor dispersion responsive to the received inputs from detector 140. For example, controller 130 may determine that odor dispersion is necessary responsive to a detection that the user is sleeping or has reached a certain sleep stage.

Controller 130 optionally instructs odor dispersion so as to control respiration of the sleeper. For example, the controller may instruct odor dispersion so as to maintain respiration within a range, for example a range of breathings within a time period or range of volume of breathings. For example, detectors 140 may detect number of breathings of the user and when the breathings are out or almost out of the range, controller 130 may instruct odor dispersion, i.e. shallow breath will increase the number of breaths in the range while deep breaths will decrease them. Alternatively or additionally, controller 130 instructs odor dispersion so as to prevent certain respiratory events, such as respiratory events that are considered as disturbing or dangerous, for example, snoring, choking or breathing suspensions. Optionally, only respiratory events at a certain range or frequency are treated. Optionally, one or more of detectors 140 detect the occurrence of such a respiratory event and controller 130 instruct odor dispersion responsive to the detection. For example, when detector 140 is a sound detector, detected sounds from the nasal may indicate snoring, which can be stopped by dispersion of odors. In addition, detection of deep breath (or increase in inhalation) may indicate that the user is about to snore and odor dispersion may be instructed. In addition, detection of no breathing sounds may indicate an apnea event which can also be treated by dispersion of odors. Alternatively or additionally, one or more detectors 140 detect that such a respiratory event is about to occur, for example by detecting deep or shallow breathings, and controller 130 instructs odor dispersion in order to prevent the occurrence of such a respiratory event. For example, when treating insomnia, detector 140 may detect that the user is about to arouse, for example by detecting that the sleeper has moved from slow wave sleep to REM sleep, or has already aroused and instruct odor dispersion. Optionally, the dispersed odors control an average volume of breath, by providing odorant more or less frequently.

Controller 130 may instruct a single odor dispersion or a cycle of odor dispersions. For example, responsive to a breathing suspension that occurred 10 min after the latest odor dispersion, controller may decide that odor should be dispersed every 9 min or less.

In some embodiments of the invention controller 130 controls respiration by instructing dispersion to influence upcoming breathings. For example, controller controls a sequence of between 1-6 breathings to be without snoring.

The controller receives inputs of the respiratory status of the user and instructs dispersion in response. For example, to treat an apnea event, to treat snoring or choking, etc. Alternatively or additionally, controller 130 controls respiration over the entire sleep period so as to control the probability of certain respiratory events during the period. For example, to reduce the probability of snoring by between 30%-70%, such as by about or more than 40%, 50% or 60% during a sleep period. Controlling the probability of certain respiratory events can be achieved by instructing odor dispersion at predefined time periods, which may or may not be connected to detections by detectors 140.

In addition, controller 130 may control respiration according to a desired reduction is snore rate and instruct odor dispersion accordingly. For example every second snore leads to odor dispersion or every second odor dispersion is with a different odorant.

In some embodiments, the inputs received from detector 140 may refrain the controller from commanding odor dispersion, even if such dispersion is applicable according to a time schedule. For example, if the user did not reach a slow wave sleep (SWS), the controller may refrain from instructing odor dispersion.

In some embodiments, when reservoir 105 includes more than one odor, controller 130 determines at 320 which odor or which type of odor should be generated. Different odors may be instructed responsive to different respiratory events. For example, snoring may lead to the generation of pleasant odors while breathing suspension may lead to the generation of unpleasant odors. In addition, yet another odor may be generated if no respiration event was detected. Alternatively, the odors are randomly chosen. Alternatively or additionally, odors are generated according to a pre-programmed sequence of odors. Optionally, the user may manually set an odor or group of odors that may be generated. Optionally, adaptation to odor is also taken into account when selecting an odor. For example, a different odor than the last odor dispersion may be selected.

At 330 the dose (or concentration) of odor is optionally determined. Different doses may be determined responsive to different respiratory events or responsive to repeated respiratory events. For example, if two breathing suspensions occur in a relatively short time frame, a greater dose of odor dispersion may be determined. Alternatively, the dose of odor is constant or a sequence of odor dose is pre-programmed. Optionally, adaptation to odor is also taken into account when determining odor dose. For example, greater doses may be determined at repeating dispersions. Alternatively or additionally, the dose of odor is pre-determined.

Controller 130 then optionally determines the time period of dispersion at 340. The time period may relate to time between odor onset and offset or to a number of breathings between odor onset and offset. Optionally, the number of breathings relates to a number of shallow or heavy breaths, for example, only heavy breaths are taken into account when measuring time period.

The time period may be determined responsive to the respiratory event or may be randomly defined. The determined time period optionally applies to a single odor dispersion. Alternatively, the determined time period applies to a sequence of odor dispersions and the time period is not re-defined for every dispersion. Alternatively, the time period of odor dispersion is fixed or set by a user or practitioner and is not determined by the controller. Alternatively, the time period of odor dispersion is constant or a sequence of time periods is pre-programmed.

Odor dispersions may be all of the same length or of different length. Optionally, each odor dispersion occurs for between 5-30 seconds, for example for 5, 10 or 20 seconds. Optionally, each odor dispersion occurs for between 3-8 breathings, such as for 5 or 6 breathings. Optionally, the length of odor dispersion also depends on the volume of odor dispersed.

Device 100 further optionally includes a learning module 180 adapted to monitor the respiratory patterns of the sleeper and learn reactions to odor dispersions. In some embodiments, learning module 180 includes a table 185 with odorants and their effect on the sleeper's respiration and/or arousal, optionally, according to sleep stage. Table 185 may further include dose of odorant, time period of dispersion and/or sleeper's adaptation to odorant. Table 185 may be updated every predefined number of odor dispersions or after an entire sleep period.

In some embodiments, learning module 180 provides inputs to controller 130 and affects determinations made in any of 320-340. Learning module 180 may comprise a number of rules on odor dispersion from which it can choose to output to controller 130.

For example, if table 185 indicates that ammonium sulfide prevents an apnea event, a rule of lavender dispersion, optionally including dose and/or time of dispersion, may be output to controller 130. For example, if table 185 indicates that a lavender provides arousal responses, module 180 may send a rule indicating that lavender should not be dispersed. For instance if table 185 indicates that a specific dose of odor is insufficient to change a respiratory pattern of the sleeper, learning module 185 may send a rule indicating that a greater dose of odor should be dispersed.

Learning module 185 may also affect a longer respiration control, for example, a sequence of odor dispersions or sleep periods. For example, learning module may indicate the start of an odor dispersion at a small dosage and monitor the effect on respiration. If the desired effect was not achieved, the learning module may indicate a greater dosage and so on and so forth till the desired effect is achieved. The same may be performed with different odorants or type of odors.

At 350, controller 130 instructs odor dispersion and generation in view of the determinations made in 320-340. In some embodiments, controller 130 is adapted to control the device in accordance with a limited number of predefined operation options. Optionally the operation options are manually adjustable by the user. For example, the device may include 5 different options for time of dispersions and 3 options for odors which are chosen by the user.

Controller 130 may be further connected to a communication unit 150. In some embodiments, upon activation of device 100, the user is logging in at a practitioner or medical center using communication unit 150, for monitoring respiration and/or odor affect on the sleeper. In some embodiments, the connection by communication unit 150 may call for a physician or ambulance when necessary. Optionally, controller 130 is also adapted to instruct activation of an alarm 160 which may cause arousal of the sleeper or people in the vicinity of the sleeper. Optionally, for example in devices which physically contact the sleeper, a vibrator is provided instead or in addition to the alarm. Optionally, the device is automatically turned off when the alarm is activated.

Device 100 further includes a power source 170 adapted to provide power to the elements of device 100. Power source 170 is optionally a battery which may be recharged. Optionally, power source 170 is purely mechanical, such as a wind-up device where a mainspring is tightened for activation. Other power sources known in the art may be used in accordance with exemplary embodiments of the invention.

A timer 180 is optionally also provided for setting the operation of the device. Alternatively, an on/off switch is provided. Alternatively, odors are automatically dispersed when events, such as respiration events or sleep stages, are detected by one or more detectors 140.

Device 100 optionally further includes a display to display the status of odor dispersions and/or the monitored detections by detectors 140. Optionally, the device also includes an input panel where the user can input the desired frequency, odorant and/or dosage of odor to be dispersed and/or characteristics to be measured or detected. Optionally, the device also has a remote control.

Although the connections of the elements of device 100 are shown in the figure, wireless connection may be used in exemplary embodiments of the invention. For example, in order to provide a small device which can fit as a nose clip, some of the elements of device 100 are optionally positioned at a distance, optionally using wireless connection.

In some embodiments, a unit 125, including reservoir 105, odor generator 110 and nozzle 120 is positioned near the nose of the sleeper, while the rest of the device elements may be positioned further away from the sleeper, for example in another room or a few meters away, such as 1 or 2 meters. Optionally, unit 125 includes only nozzle 120 which is connected by a long tube to the rest of the device. Placing unit 125 away from the rest of the device may assist in avoiding noise or lights (LEDs) of the device to affect arousal or wake-up of the sleeper.

Optionally, one or more detectors 140 are also provided in unit 125. Optionally, some of detectors 140 are positioned in unit 125, while other detectors are separately provided. For example, a sound detector may be positioned near the nose of the sleeper while a respiratory movement detector will be positioned beneath the mattress or bed sheet. In some embodiments, controller 130 is also included in unit 125.

FIGS. 2A-2C are exemplary embodiments of devices for controlling respiration during sleep integrated near the nose of a sleeper.

FIG. 2A illustrates a device 101 in a bed pillow. In the embodiment of FIG. 2A, the odorant is liquid or volatile. Optionally, device 101 comprises a cover which prevents the odorant from reaching the user, when no odor dispersion is instructed.

FIG. 2B illustrates a device 102 as a nose-ring. In the embodiment of FIG. 2B, the odorant is optionally dispersed as an air puff. Alternatively, device 102 continuously blows air and a block of odorant is embedded in the airflow when dispersion is instructed.

FIG. 2C illustrates a device 103 in the form of a bed lamp. In the embodiments of FIG. 2C, the odorant may be dispersed as an air puff or as a liquid. Optionally, odor is evaporated using an electrical heater. Optionally, the device includes a tube that is attached to the nose of the sleeper where the odorants will be released. The tube is optionally connected such that it does not move during sleep, for example by being attached to the back of the sleeper's head.

Unless otherwise described, devices 101, 102 and 103 contain similar elements and functions as described herein for device 100.

Figure 4:
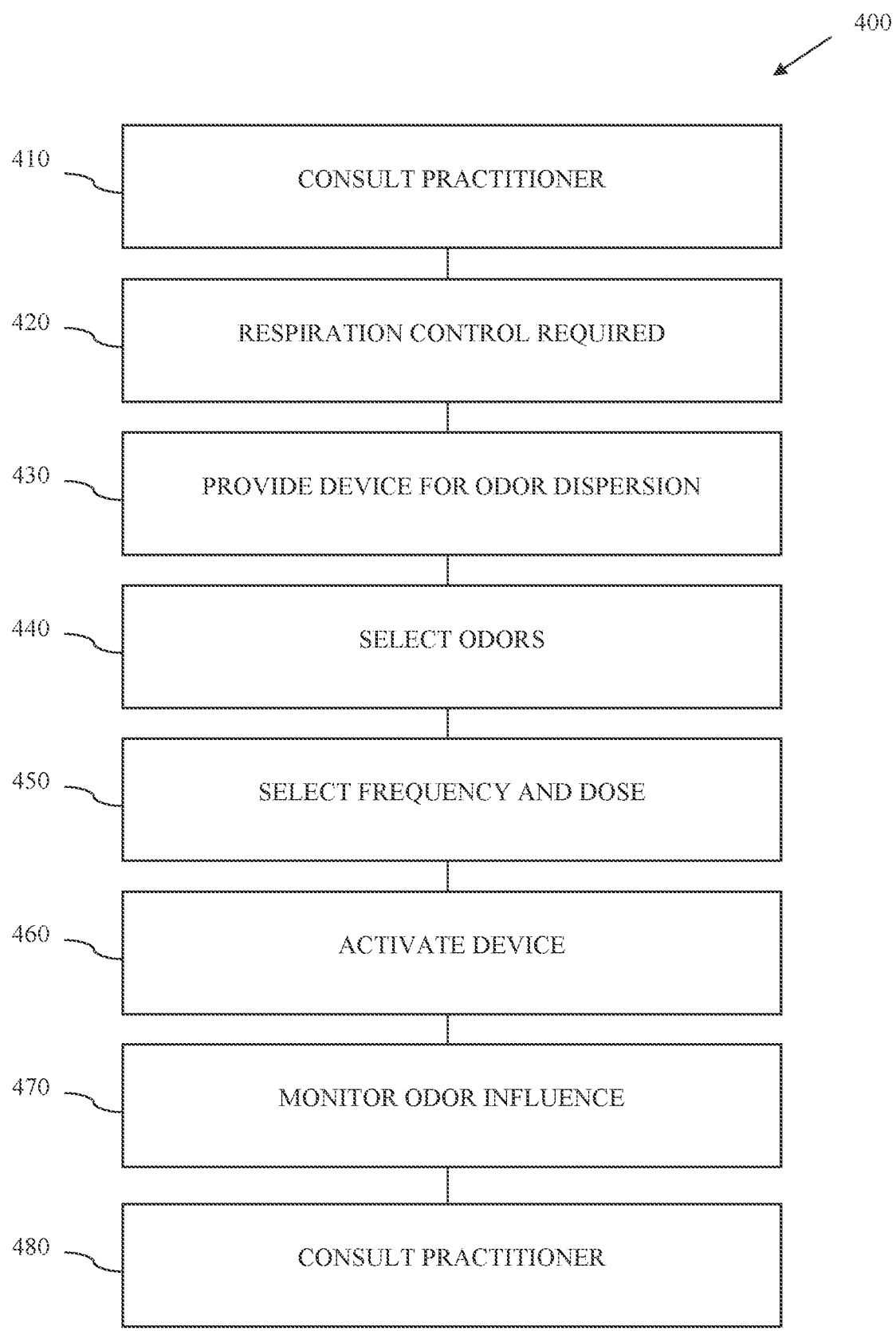
FIG. 4 is a flowchart of a method of controlling respiration in accordance with some embodiments of the invention.

FIG. 4 is a flowchart of a method 400 for respiration control in accordance with some embodiments of the invention.

At 410 a user consults a practitioner following complaints on sleep disorders. The complaints may be complaints by the user's surrounders, such as snoring or complaints by the user himself, such as frequent arousals. Optional, the complaints relate to medical state of the user, such as apnea or any other breathing disorder.

At 420, the practitioner determines that respiration control during sleep is required in order to aid the user. Optionally, the practitioner instructs a treatment by odor dispersion. Alternatively, the practitioner first instruct other treatment means, such as for example sleep-up for apnea treatment, and instructs odor treatment only after other treatments have failed. Optionally, the practitioner instructs respiration control as described with respect to method 300 above.

In some embodiments, it is determined that a treatment of a certain time period is necessary. In other embodiments, no time period for the treatment is determined and the treatment is ongoing, optionally, for life.

An odor dispersion device is provided at 430. Optionally, device 100 is provided for odor dispersion. Alternatively, other odor dispersion means known in the art may be used.

Odors for dispersion are selected at 440. In some embodiments, odors are selected after a survey of the effect of the odor on the user's respiration. For example, a plurality of odors are inhaled by the user and the user's respiration response thereto is measured. Optionally, odors which provide respiratory rejection type responses, such as decreased inhalation and/or decreased exhalation, are used. For example, for apnea treatment, any of vanillin, lavender, ammonium sulfide and/or vetiver may be used. Optionally, the pleasantness of the odor to the user and/or to others sleeping near the user are also taken into account.

In some embodiments, only odors which do not induce arousal or wake-up responses are selected. Optionally, only olfactory or mild trigeminal odors are selected. Optionally, one or more of the above criteria are taken into account when selecting odors.

In some embodiments, a table, such as table 185 described above, with odorants and their effect on the user's respiration and/or arousal is created, optionally, according to sleep stage. The table then assists in selecting odorants for dispersion responsive to physiological measurements, such as respiration events and/or sleep stage.

In some cases, a user acquires an odor dispersion device without consulting a practitioner.

At 450 the frequency and dose of odor dispersion is selected. Optionally, a sequence of odor dispersion is selected. Alternatively, each odor dispersion is separately selected according to physiological measurements made and/or according to information in the table.

The device is activated at 460, optionally, at the sleep time of the user.

Influence of the odor dispersions are monitored at 470. The influence on several physiological characteristics may be monitored. For example, overall respirations, nasal and oral respirations can be measured by respiratory belts or by a nasal masks. Arousal responses may be measured according to measurements of EEG and EMG by electrodes. Also Electroocculogram, and Electrocardiogram (ECG) may be measured using electrodes. Alternatively arousal responses may be measured using EMG or EKG alone. Optionally also Blood oxygation (SpO2) is measured by finger clip sensor. Optionally, sleep stage is detected by electrodes or a helm. Optionally, the users wears a cap for measuring physical characteristics and/or disperse odors.

At 470 the practitioner is consulted again to discuss the influence of the treatment. The table and measured physiological characteristics are examined. 440 and 450 may be updated in view of the results examined.

In some embodiments, odor influence is monitored during the sleep period and odorant, dose and/or dispersions frequency and/or dose may be changed in view of the monitored characteristics. Alternatively, influence is examined after one or more sleep periods, for example after between 20-40 odor dispersions. Odorant, dose and/or dispersions frequency and/or dose are then optionally changed for the next sleeping period.

For example, if it is determined that vetiver provides arousal responses, vetiver may be removed from the odorants used. Also, if it is determined that vanillin has a better effect on stage 2 sleep, vanillin may be used when stage 2 is reached. In addition, if it is determined that after 2 similar odor dispersions the user adapts to the odorant and a lower or no respiratory response is received, odors may be changed after every dispersion.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion. The inventors of the present application made the following experiment of odor influence on respiration during sleep.

Example 1

Participants

Forty-five healthy subjects (21 women and 24 men) ranging in age from 23 to 36 years (M=27.2±2.28 years) participated in the study after providing informed consent to procedures approved by the Committee for Protection of Human Subjects at the Assuta hospital. Subjects were screened for abnormal sleep habits and history of nasal insults. Exclusion criteria were irregular breathing pattern, insufficient sleeping time, and use of medication or demonstration of sleep apnea syndrome with respiratory disturbance index >10. Nine subjects failed to meet the study criteria and were therefore excluded from analysis.

Odorants

Four odorants composed of both molecules and blends were used: undiluted lavender oil (Sensale) (n=14) considered pleasant and mildly trigeminal, undiluted vetiver oil (Givaudan) (n=10) considered unpleasant and mildly trigeminal, 3% v/v vanillin (CAS 121-33-5, Sigma-Aldrich) (n=15) considered pleasant and pure olfactory, and 1% v/v ammonium sulfide (CAS 12135-76-1, Sigma-Aldrich) (n=6) considered unpleasant and pure olfactory.

Odorant Delivery

Odorants were delivered with a computer-controlled air dilution olfactometer built according to principals described in Sobel et al. 1997; Johnson and Sobel 2007 which are incorporated herein by reference. Room air (3 Liter per minute) was mixed with the odorized air (3 liter per minute), resulting in odor concentration of 50%. The odorant line culminated at a small nasal mask that was subserved by a vacuum line pulling at the same rate of airflow. This provided an odor environment at the nose where odorant onset and offset occurred within 2 and 260 ms, respectively, with no visual, auditory, tactile, humidity, or thermal cues as to the alteration. In other words, the odorant stimulus was not a puff of air but rather a block of odorant embedded within an airflow that was constant for the duration of the study. The olfactometer itself was located in a room adjacent to the sleep room, and only the airflow tubing crossed into the sleep room via a wave guide within the stainless steel-coated wall. This provided additional separation from any possible visual or auditory stimulation associated with the olfactometer (e.g., LEDs on its front panel, etc.).

Polysomnography and Sleep Scoring

Physiological measurements were recorded using a Power-Lab 16SP Monitoring System (ADInstruments) running off a Macintosh G4 computer using a sampling rate of 1000 Hz and a 50-Hz notch filter to remove electrical artifacts. For all measures dependent on electrodes, the scalp surface was cleaned with mild abrasive gel (Nuprep gel, Aurora) in order to assist in lowering impedance at the electrode site. For pasted electrodes on the rest of the body, the skin surface was also first cleaned with alcohol. The following measures were recorded:

Electroencephalogram (EEG) was obtained through 2 circular electrodes (0.9 mm diameter) that were located at positions C3 and C4 according to the 10-20 system and were referenced to electrodes on the opposite mastoids (A2 and A1, respectively). Signals were amplified using a preamplifier (Octal Bio Amp ML138, ADInstruments).

Electroocculogram was obtained through 2 circular Ag/AgCl conductive adhesive electrodes (0.9 cm diameter), placed 1 cm above and laterally of each eye, and referenced to electrodes on the opposite mastoids (A2 and A1, respectively). Signals were amplified using a preamplifier (Octal Bio Amp ML138, ADInstruments).

Electromyogram (EMG) was obtained through 2 circular Ag/AgCl conductive adhesive electrodes (0.9 cm diameter). The electrodes were located bilaterally adjacent to the submentalis muscles. Signals were amplified using a preamplifier (Octal Bio Amp ML138, ADInstruments).

Electrocardiogram (ECG) was obtained through 3 circular Ag/AgCl conductive adhesive electrodes (0.9 cm diameter). Electrodes were placed on both the left and the right sides of the abdomen, and a ground electrode was placed on the left foot. Signals were amplified using a preamplifier (Bio Amp ML132, ADInstruments).

Blood oxygination (SpO2) was measured with an oxymeter (MLT321 SpO2 Finger Clip Sensor, ADInstruments) embedded within a finger clip placed on the left index finger.

Overall respiration was computed as a reflection of changes in thoracic respiration and abdominal respiration circumference measured using 2 piezoelectric respiratory belt transducers (1132 Pneumotrace II, UFI).

Nasal and Oral respiration was measured using separate pneumotachometers (high-sensitivity flowmeter model #4719, Hans Rudolph, Inc.) that were attached in line with the vent ports of the mask. The pneumotachometer differential pressure was measured and converted to a voltage signal using a spirometer (ML141, ADInstruments) that delivered the voltage to the instrumentation amplifier.

Sleep stages were scored off-line according to the R and K criteria (Rechtschaffen and Kales 1968). An abrupt change in EEG frequency and/or brief increase in EMG amplitude for more than 3 s or over 15 s were classified as arousal or wake-up, respectively, as defined by the atlas task force of the American Sleep Disorder Association (AAoSMTF 1992). An arousal or wake-up was attributed to the odor stimuli if they occurred anywhere from odor onset to 30 s following odor offset (Stuck et al. 2007). Scoring for respiratory events, apnea and hypopnea, were according to the American Academy of Sleep Medicine (AAoSMTF 1999).

The effects of odorants on 4 breath parameters were tested: breath mean airflow velocity, breath maximum airflow velocity, breath volume, and breath duration. Breath volume was calculated by the trapezoidal Reimann sum method (Johnson et al. 2006). Breaths were aligned in time by setting the point at which the breath passed from the expiratory phase to the inspiratory phase as time 0.

Any of the above measurements can be used according to exemplary embodiments of the present invention.

Procedures

Subjects arrived at the olfaction sleep laboratory at a selfselected time, based on their usual sleep time, typically ~11:00 PM. After providing informed consent, subjects were led to the experimental room. This room was coated in stainless steel in order to prevent ambient odor adhesion and supplemented with high-efficiency particulate air and carbon filtration to further assure an odor-free environment. Subjects first rated the intensity and pleasantness of the odorant using a visual analog scale (VAS). The VAS consisted of a line without any tick marks (14 cm long), with only the extremes marked as reflecting "very" or "not at all" (in Hebrew). After fitting of the polysomnography devices and assuring a comfortable positioning within the bed, subjects were left alone in the darkened room to be observed from the neighboring control room via IR video camera and 1-way observation window.

The experimenters observed the real-time polysomnography reading, and 20 min after they determined that the subject had entered stage 2 sleep, they initiated the experimental protocol that from this point on was computer controlled. Every 9, 12, or 15 min (randomized), the olfactometer generated a 5-, 10-, or 20-s (randomized) odor stimulus. This resulted in 21-37 odorant presentations per night. Upon spontaneous morning wake-up, subjects again rated the intensity and pleasantness of the odorant and were then debriefed, paid, and released.

Statistics

The obtained ratings for the respective odorant qualities were analyzed to test for differences between odorants in perception before and after the night. Odorant ratings were compared using a repeated measures analysis of variance (ANOVA) within Statistica software (StatSoft, Inc.). The ANOVA analysis was followed by contrast t-tests to test the difference between each 2 odorants. A P value of less than 0.05 was considered significant.

The number of arousals attributed to an odor divided by the total number of odor presentations was the "odor arousal frequency." The number of arousals attributed to an odorless baseline period (containing an equal flow of clean air) divided by the total number of odor presentations was the "baseline arousal frequency." Wake-up frequencies were calculated in the same manner. Frequencies were calculated for each subject and for each sleep stage. Frequencies of arousals and wake-ups were compared between and across sleep stages per odorant in a repeated measures ANOVA.

Averages of respiration measurements for inhalation, exhalation, and inhalation/exhalation ratio in the 30 breaths before odor onset were compared with the averages of respiration measurements for inhalation, exhalation, and inhalation/exhalation ratio for each one of 6 breaths after odor onset across sleep stages per odorant and for all odorants together. This analysis was corrected for the 6 comparisons using a Bonferroni correction. Respiratory measurements were compared between sleep stages per odorant in a repeated measures ANOVA.

Results

Psychophysical Results

Figure 5A:
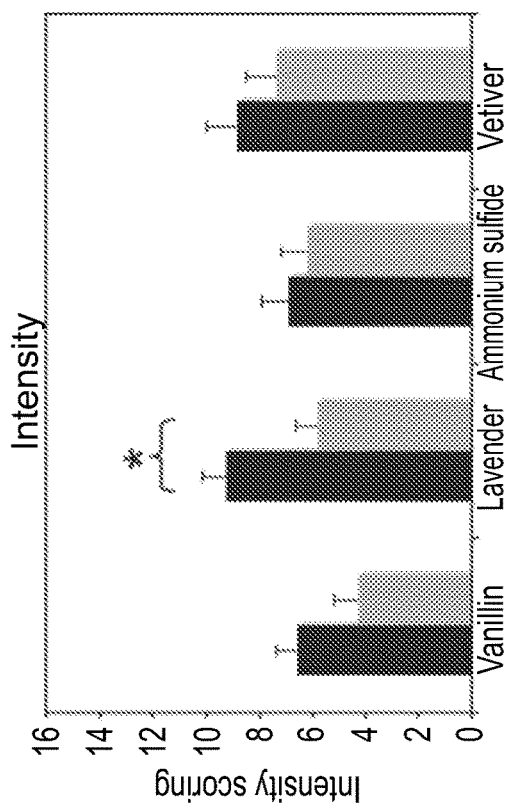
FIGS. 5A-5B are graphic illustrations of pleasantness (FIG. 5A) and intensity (FIG. 5B) scoring from the evening (before) and the morning (after) for the 4 odorants used in an experiment according to some embodiments of the invention.
Figure 5B:
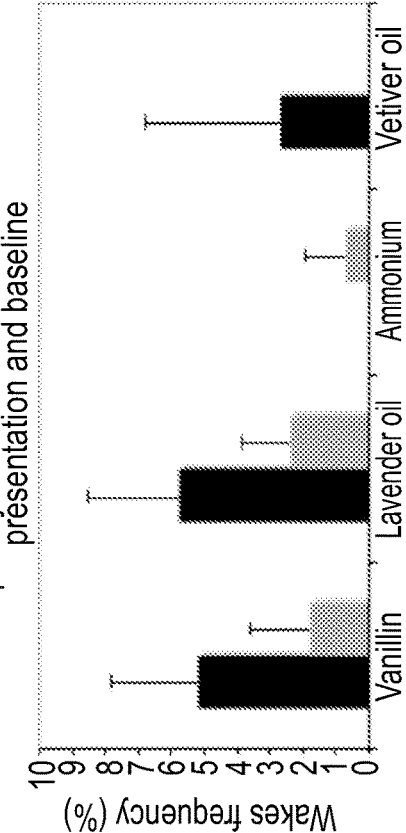

As intended, the odors differed in pleasantness [average across evening and morning: vanillin 9.0±2.3, lavender oil 8.1±2.1, ammonium sulfide 6.9±1.2, and vetiver 4.6±3.1; $F(3,30)=6.34$, $P<0.005$] (FIG. 5). Lavender oil and vanillin were perceived as more pleasant than vetiver oil [all $F(1,14)>7.09$, $P<0.02$], and vanillin was perceived also as more pleasant than ammonium sulfide [$F(1,16)=5.89$, $P<0.03$]. There were no significant differences in odor intensities [averages across evening and morning scores: vanillin 5.4±2.2, lavender oil 7.5±1.7, ammonium sulfide 6.6±2.1, and vetiver 7.9±2.8; $F(3,30)=2.4$, $P<0.08$].

Odor pleasantness did not shift as a result of the nights' exposure for any odorant [evening scores: vanillin 10.0±2.9, lavender oil 7.9±2.5, ammonium sulfide 7.1±1.2, and vetiver 4.3±3.0; morning scores: vanillin 8.1±4.3, ammonium sulfide 6.1±2.0, lavender oil 8.2±2.6, and vetiver 3.8±2.5; all $F(1,11)<1.37$, $P>0.2$]. In contrast, lavender oil intensity was perceived as weaker in the morning (5.8±2.3) than in the evening [9.3±2.5, $F(1,7)=9.11$, $P<0.02$], and a similar trend was observed for vanillin [evening score: 6.6±2.7, morning score: 4.25±2.7; $F(1,11)=4.21$, $P<0.06$].

There was no change in the intensities of ammonium sulfide and vetiver oil [evening scores: ammonium sulfide 6.9±2.4 and vetiver oil 8.8±3.4; morning scores: ammonium sulfide 6.2±2.4 and vetiver oil 7.4±3.4; all $F(1,7)<1.72$, $P>0.3$].

Odorants Did not Arouse or Wake

The odorants vanillin (n=12 after exclusions), lavender oil (n=13 after exclusions), and ammonium sulfide (n=5 after exclusions) were initially tested. For vanillin, there was no effect of odor on wake-up [$F(1,11)=2.23$, $P<0.16$], regardless of sleep stage [$F(2,22)=0.009$, $P<0.99$], and no effect of odor on arousal [$F(1,11)=2.93$, $P<0.12$], regardless of sleep stage [$F(2,22)=1.98$, $P<0.16$]. For lavender oil, there was no overall effect on arousal [$F(1,12)=0.13$, $P<0.72$], with a sleep stage effect [$F(2,24)=8.68$, $P<0.001$] reflecting increased arousal in stage 2 sleep compared with other sleep stages.

Figure 6A:
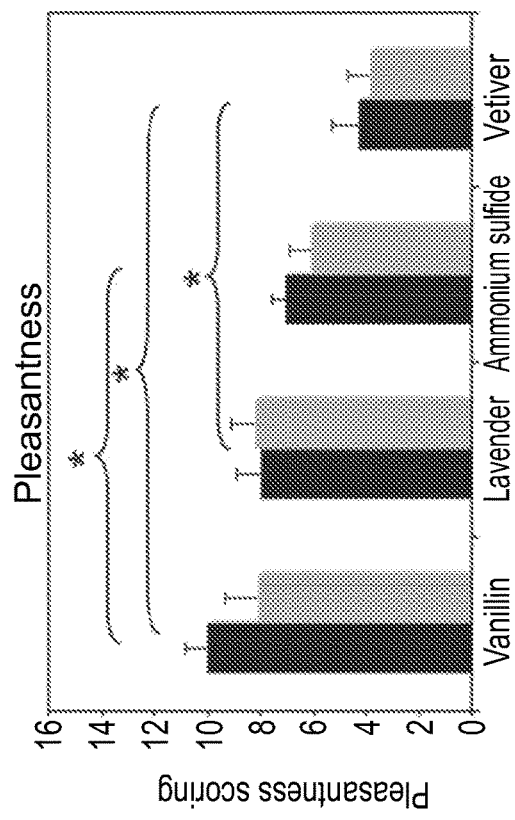
FIGS. 6A-6B are graphic illustrations of (FIG. 6A) Frequency of arousals associated with odor and baseline (clean air presented) in 4 odorants and (FIG. 6B) Frequency of wake-ups associated with odor and baseline (clean air presented) in 4 odorants used in an experiment according to some embodiments of the invention.
Figure 6B:
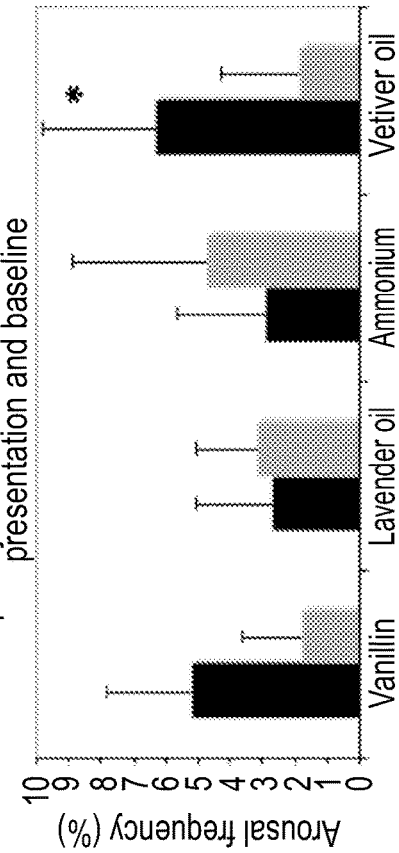
Figure 8A:
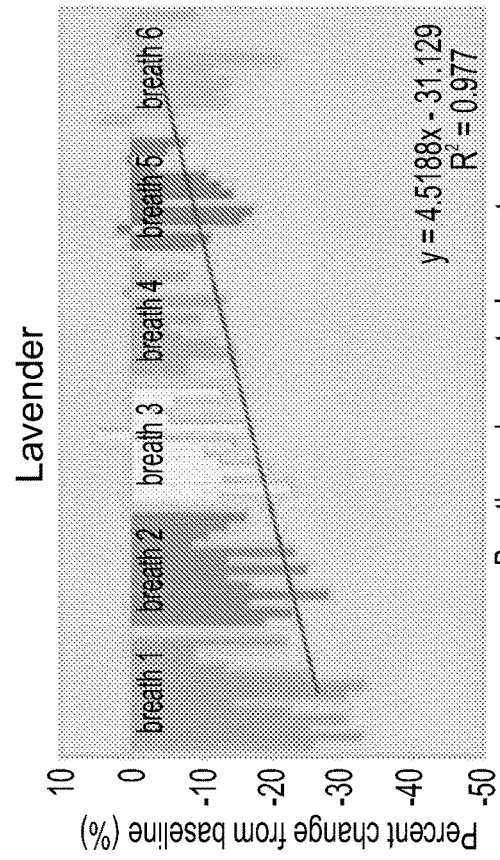
FIGS. 8A-8D are graphic illustrations of percent change from baseline in the inhale/exhale volume ratio in 6 consecutive breathes following 1 of 4 odors used in an experiment according to some embodiments of the invention.
Figure 8B:
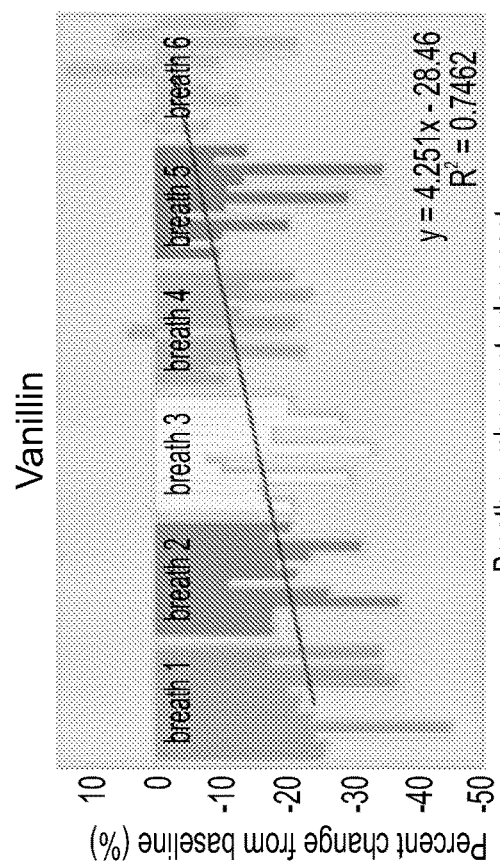
Figure 8C:
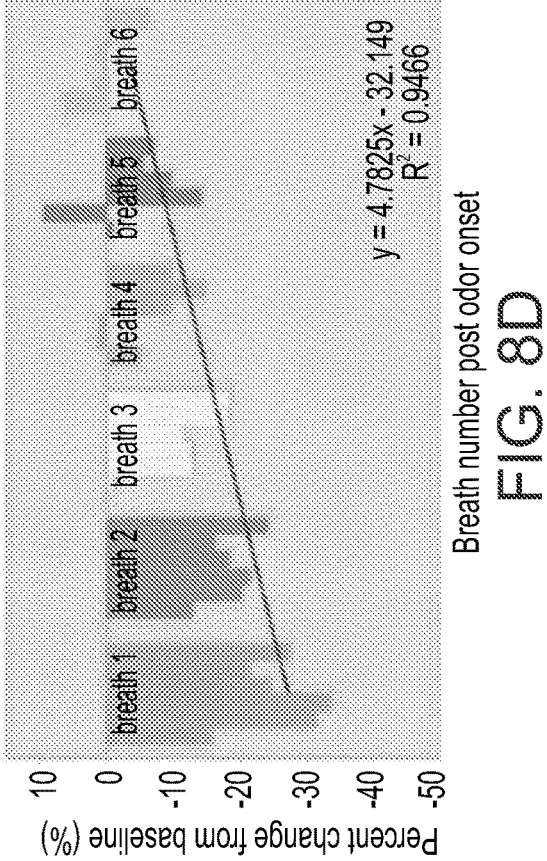
Figure 8D:
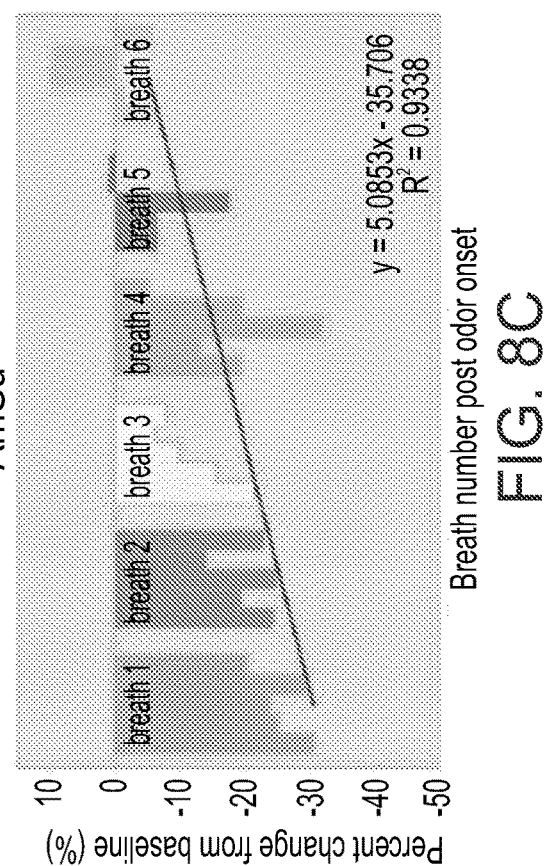

There was a trend toward an effect on wake-ups [$F(1,12)=3.53$, $P=0.084$], whereby lavender oil lowered the frequency of wake-ups, and a significant interaction between wake-up rates and sleep stage [$F(2,24)=3.37$, $P<0.03$], reflecting increased wake-up in stage 2 sleep in the presence of odor compared with other sleep stages and baseline. For ammonium sulfide, there was no effect of odor on wake-up [$F(1,4)=1.0$, $P<0.37$], regardless of sleep stage [$F(2,8)=1.0$, $P<0.41$], or arousal [$F(1,4)=0.56$, $P<0.49$], regardless of sleep stage [$F(2,8)=0.45$, $P<0.64$] (FIG. 6, Table in FIG. 7). Consistent with these results, ECG and blood oxygenation measurements were not influenced by odor presentation [ECG levels at baseline=57.96±7.34 beats per minute (BPM), ECG levels after odor presentation=58.04±7.37 BPM; $F(1,26)=0.23$, $P<0.6$; blood oxygenation at baseline 97.04±1.22, blood oxygenation after odor presentation 97.06±1.23; $F(1,23)=0.35$, $P<0.56$]. The subjects' blood oxygenation levels during wake-up were 97.66±1.12% and total night average was 96.84±1.56%.

Odors Influenced Respiratory Patterns in Sleep

The inhale/exhale volume ratio was significantly smaller following odor presentation in comparison to baseline for vanillin (n=12 following exclusions), ammonium sulfide (n=5 following exclusions), and lavender oil (n=13 following exclusions) across all sleep stages (FIG. 8, Table in FIG. 9). This effect was most pronounced for the first breath following odorant onset [$F(1,35)=384.51$, $P<0.0001$] and then decreased in a nearly linear fashion until it was on the border of significance (Bonferroni corrected) at the sixth breath after odorant onset [$F(1,35)=7.87$, $P<0.0081$] (FIG. 8). For all odorants, there was no difference in respiration volume ratio across sleep stages [vanillin $F(2,22)=2.61$, $P<0.1$; lavender oil $F(2,24)=3.00$, $P<0.07$; ammonium sulfide $F(2,8)=0.24$, $P<0.79$].

Figure 10A:
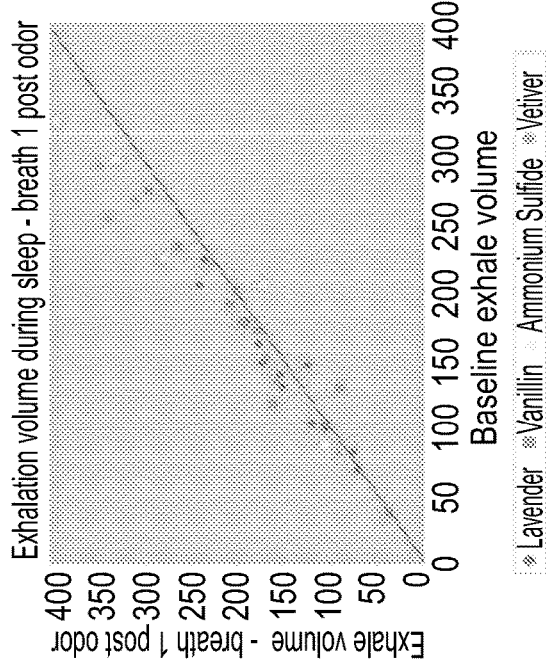
FIGS. 10A-10B are a graphic illustration of breath inhale (FIG. 10A) and exhale (FIG. 10B) volume in the first breath following odor onset (Y axis) and baseline without odor (X axis) used in an experiment according to some embodiments of the invention.
Figure 10B:
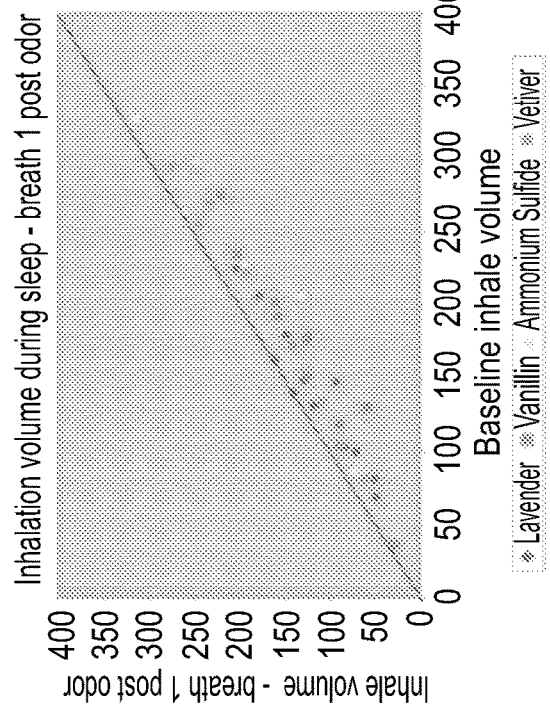

Breath inhalation and exhalation volume were also separately examined. Inhalation volume decreased significantly following odor onset for all 6 breaths after odor onset across the 3 odorants [all $F(1,29)>14.2$, $P<0.0007$]. Exhalation volume increased significantly in comparison to baseline for only the first breath after odor onset across the 3 odorants [$F(1,29)=9.36$, $P<0.005$] (FIG. 10, Table in FIG. 9).

The influence of odors on respiratory patterns in sleep reflected a temporary increase in net exhalation.

The after odorant decrease in nasal inhalation and increase in nasal exhalation may have resulted from 2 alternative scenarios. In the first scenario, the odorant-induced temporary increase in the net nasal exhalation may have relied on the lung's air reserve. The second alternative is that, although oral respiration typically reflects only; 4% of overall respiration in sleep (Fitzpatrick et al. 2003), the odorant may have changed the balance between nasal and oral breathing such that oral inspiration increased. Under this scenario, the increase in nasal exhalation reflected an increase in oral inspiration rather than the exhalation of air stored in the lungs. The above data could not discriminate between these alternatives because it relied on accurate measurement of nasal respiration alone. An additional control group of 10 subjects were studied using the odorant vetiver oil that in addition to the nasal mask were fitted with an oral mask in order to accurately measure oral and nasal respiration simultaneously.

Regarding the effects of the odorant on sleep, the results with vetiver oil were similar to those with the 3 previous odorants. Seven subjects had full polysomnography data, and in these, there was a significant decrease in arousal frequency following odorant presentation [$F(1,6)=28.13$, $P<0.001$], regardless of sleep stage [$F(2,12)=0.95$, $P<0.41$], and no change in wake-up frequency [$F(1,6)=1.29$, $P<0.29$], regardless of sleep stage [$F(2,12)=0.86$, $P<0.45$] (FIG. 6, Table in FIG. 7).

Figure 11:
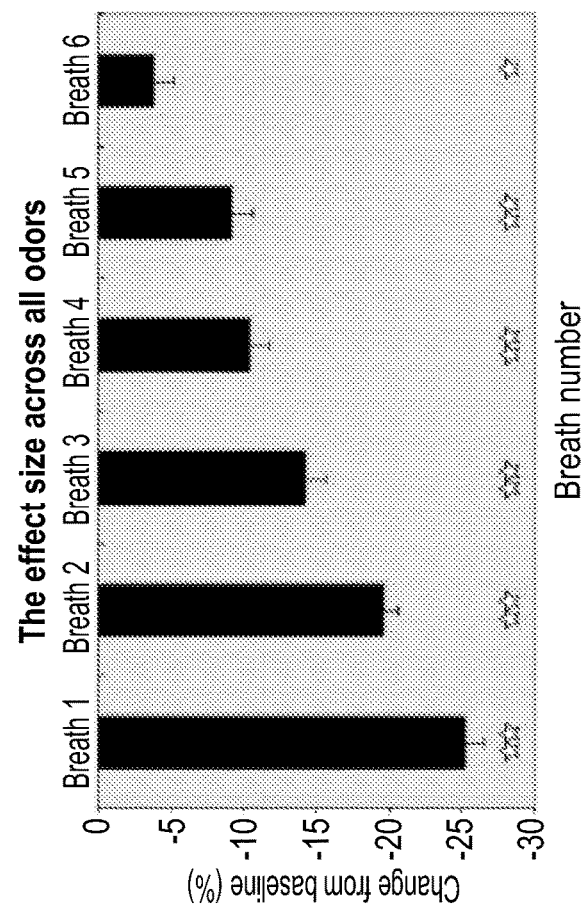
FIG. 11 is a graphic illustration of percent change from baseline of the inhale/exhale volume ratio for 6 consecutive breathes following odor onset performed in an experiment according to some embodiments of the invention.

Regarding the effects of the odorant on respiration, only 0-18% of overall after odorant respiration was oral, and it was indeed nasal respiration that carried the previously observed effects, whereby the odorant reduced inhale/exhale volume ratio across all sleep stages (FIG. 8, Table in FIG. 7) (1 subject had a stuffed nose and was therefore excluded from this analysis). In analyzing the nasal respirations, this effect was significant for 3 consecutive breathes following odor onset [all $F(1,5)>22.34$, $P<0.006$], regardless of sleep stage [$F(2,10)=1.127$, $P<0.36$]. In all 4 odorants, there was a ~30% change in inhale/exhale volume ratio in the first breath following odor onset (FIG. 11). Similar to the other odorants, the effects in vetiver oil were a result of a decrease in inhalation and increase in exhalation volume that remained significant for 2 breaths following odor onset [all $F(1,5)>11.02$, $P<0.02$]. In other words, the change that was found in respiration pattern during sleep reflected a temporary increase in net nasal exhalation that relied on the lung's air reserve.

Although all odorants tested had a similar type of influence on respiration, the results were combined using vetiver oil with those using ammonium sulfide in order to allow a better test for any influence of odorant valence on respiration in sleep. This combination generated 1 group of 11 subjects tested with unpleasant odorants (vetiver oil and ammonium sulfide) and 2 separate groups of 12 (vanillin) and 13 (lavender oil) subjects tested with pleasant odorants. No difference in the effect size of the inhale/exhale volume ratio across the odorants [all $F(2,33)<2.23$, $P>0.12$] were found, and follow-up tests revealed no significant differences in either inhale or exhale change across valences [all $F(2,33)<1.37$, all $P>0.2$].

To further examine the influence of odor valence on respiratory volume ratio, comparison was made between pleasant odorants (vanillin and lavender oil) and the unpleasant odorants (vetiver oil and ammonium sulfide). It was found that the inhale/exhale volume ratio was not influenced by valence [all $F(1,32)<5.59$, P=not significant following correction].

Moreover, to further examine the influence of trigeminality on respiratory volume ratio, comparison was made between mildly trigeminal odorants (lavender oil and vetiver oil) and pure olfactants (vanillin and ammonium sulfide). It was found that the inhale/exhale volume ratio was greater for pure olfactants only at the fourth breath after odorant onset [pure olfactants=0.15±0.08, mild trigeminal odors=0.07±0.05; $F(1,32)=13.1$, $P<0.001$].

Finally, the entire above analysis depicted the results considering the measure of breath volume. Consistent with previous studies (Youngentob et al. 1987), breath volume was correlated to the 3 other breath measures (volume and duration, r=0.73, $P<0.0001$; volume and maximum airflow velocity, r=0.57, $P<0.07$; volume and mean airflow velocity, r=0.56, $P<0.03$). Repeating the analysis with either of these respiratory measures revealed a nearly identical picture.

Example 2

One male participant at the age 22 participated in this study. The participant suffered from snoring but did not suffer from apnea. Two blends of odorants were used: undiluted Rotten Fish (Sensale, Ramat-Gan, Israel) and undiluted Toilet deodorizer. The dispersion of the odors lasted three second and occurred every 25 second to 5 minutes in a randomized order. 3 liters of odorant were mixed with 3 liters of air, resulting in odor concentration of 50%.

Figure 12:
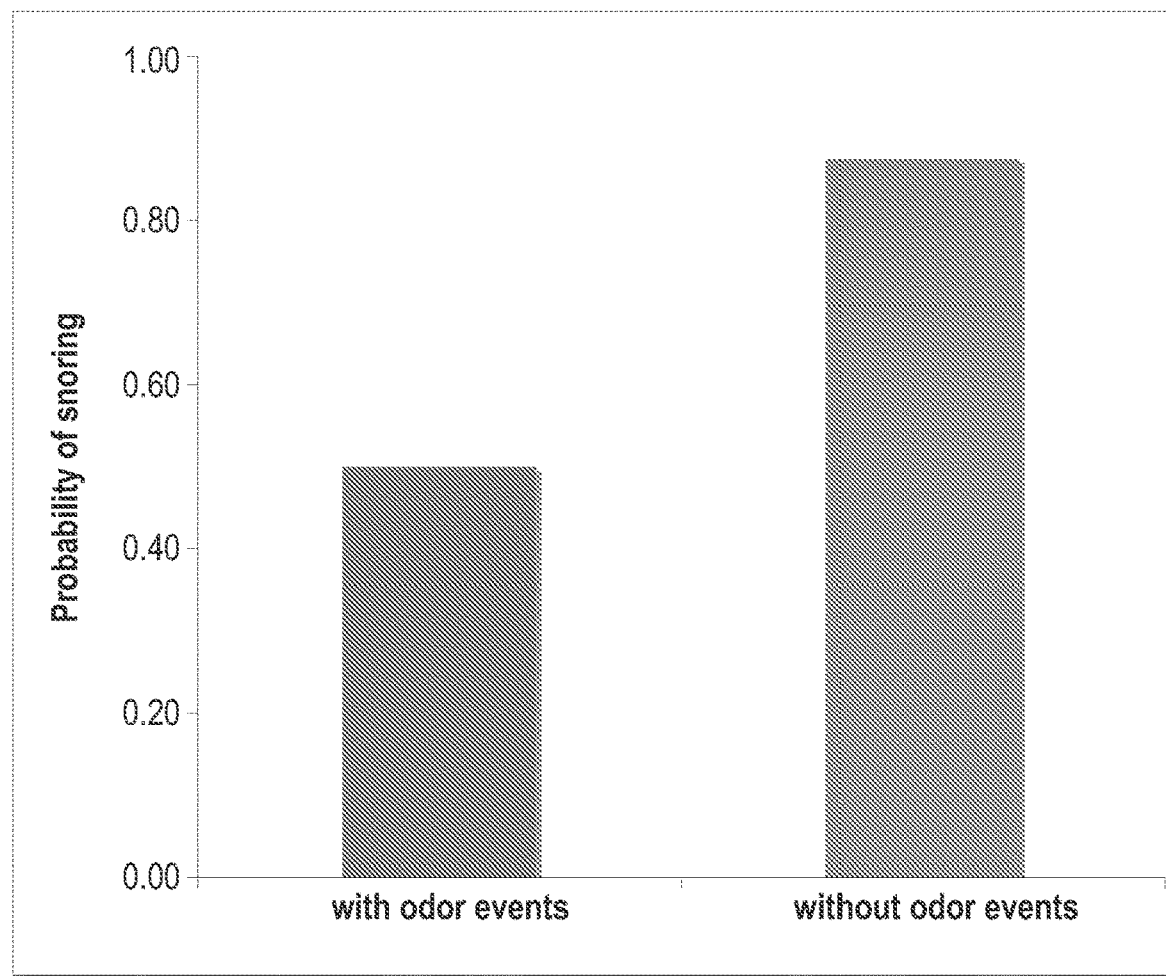
FIG. 12 is a graph illustration of probability of snoring with and without odor dispersion performed in another experiment according to some embodiments of the invention.

The results of this study show that repeated dispersion of odor during a sleep period significantly reduced snoring. FIG. 12 shows the probability of snoring with and without odor dispersion. The probability of snoring of the participant in the base line was 90% and repeated odor dispersion reduced the probability to about 50%.

Figure 13:
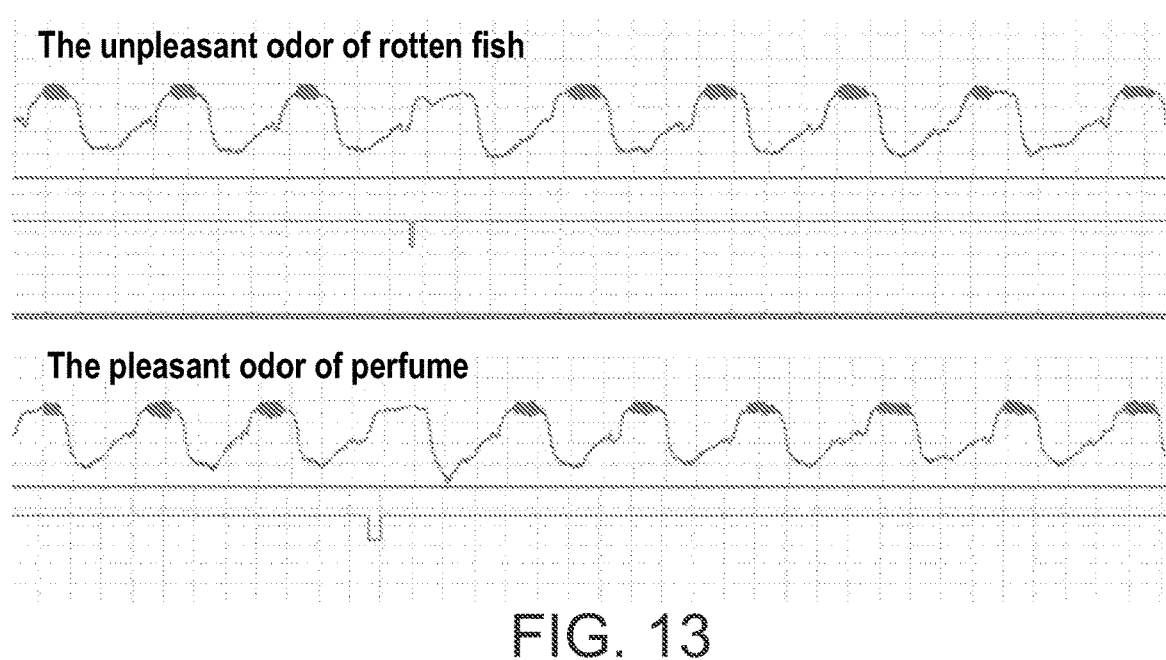
FIG. 13 is a graph illustration of respiratory cycles of the experiment of FIG. 12 according to some embodiments of the invention.

FIG. 13 illustrates respiratory cycles of the participant, where the "noise" at the respirator cycles reflect snoring. The line below the graph reflects odor dispersion. It was shown that there was no snoring for the first breath after odor dispersion of both rotten fish and perfume, i.e., both pleasant and unpleasant odors.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of providing an odor during sleep, the method comprising:

monitoring physiological characteristics of a sleeper during a sleep period; and automatically dispersing an odor, in response to said monitoring, and changing a type of said odor to be dispensed at least once during the sleep period.

2. A method according to claim 1, further comprising:
(a) monitoring respiration sound and/or respiration movement of said sleeper;
(b) monitoring arousal of said sleeper; and/or
(c) monitoring respiratory responses to said dispersing.

3. A method according to claim 1, further comprising selecting an odor for dispersion responsive to said monitoring.

4. A method according to claim 1, further comprising selecting a time length of odor dispersion responsive to said monitoring.

5. A method according to claim 1, wherein controlling respiration comprises controlling respiration without inducing arousal.

6. A method according to claim 1, wherein controlling respiration comprises increasing inhalation of at least one breath following odor dispersion.

7. A method according to claim 1, wherein said monitoring occurs after between 20-40 odor dispersions.

8. A method of claim 1, wherein said repeatedly dispersing is in response to breathing suspension.

9. A method of claim 1, comprising monitoring snoring sounds of said sleeper, wherein said repeatedly dispersing is in response to said snoring sounds.

10. A device for providing an odor during sleep, the device comprising:
an odorant reservoir having a plurality of different odors;
an odor disperser adapted to disperse an odor from said odorant reservoir;
a sensor configured for sensing physiological characteristics of a sleeper;
a controller configured for monitoring signals from said sensor, for controlling the odor dispenser to disperse said odor, and for changing a type of said odor to be dispensed at least once during a sleep period of the sleeper, responsive to said monitored signals.

11. A device according to claim 10, wherein the controller is further configured for controlling respiration of the user over a sleep period by repeatedly instructing the odor dispersion to disperse an odor during said sleep period.

12. A device according to claim 10, further comprising a respiration detector.

13. A device according to claim 10, wherein the controller is further configured for selecting a dose of odor for dispersion.

14. A device according to claim 10, wherein said controller is configured to receive said detections after between 20-40 odor dispersions.

15. A device according to claim 10, wherein said controller is configured to repeatedly disperse said odor in response to breathing suspension.

16. A device according to claim 10, comprising an additional detector configured to monitor snoring sounds, and said controller is configured to repeatedly disperse said odor in response to said snoring sounds.

17. A device according to claim 10, comprising a learning module, wherein said controller is configured for changing said type of said odor based on input from said learning module.

* * * * *